United States Patent
Dunki-Jacobs et al.

(10) Patent No.: US 11,452,574 B1
(45) Date of Patent: Sep. 27, 2022

(54) SYSTEMS AND METHODS FOR PREVENTING TISSUE MIGRATION IN SURGICAL STAPLERS

(71) Applicant: Standard Bariatrics, Inc., Cincinnati, OH (US)

(72) Inventors: Adam R. Dunki-Jacobs, Cincinnati, OH (US); Mark S. Ortiz, Milford, OH (US); Jonathan R. Thompson, Cincinnati, OH (US); Richard P. Nuchols, Williamsburg, OH (US); Caleb J. Hayward, Goshen, OH (US); Robert T. Means, III, Cincinnati, OH (US); Saylan J. Lukas, Cincinnati, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 0 days.

(21) Appl. No.: 17/700,599

(22) Filed: Mar. 22, 2022

Related U.S. Application Data

(60) Provisional application No. 63/164,837, filed on Mar. 23, 2021.

(51) Int. Cl.
  *A61B 17/064* (2006.01)
  *A61B 90/00* (2016.01)
  *A61B 17/072* (2006.01)

(52) U.S. Cl.
  CPC ........ *A61B 90/03* (2016.02); *A61B 17/07207* (2013.01); *A61B 2017/07257* (2013.01);
  (Continued)

(58) Field of Classification Search
  CPC ................ A61B 17/07207; A61B 2017/07214
  See application file for complete search history.

(56) References Cited

U.S. PATENT DOCUMENTS

| 348,126 A | 3/1907 | Roosevelt |
| 1,413,896 A | 4/1922 | Brix |

(Continued)

FOREIGN PATENT DOCUMENTS

| CA | 2663002 A1 | 10/2009 |
| EP | 140552 A2 | 5/1985 |

(Continued)

OTHER PUBLICATIONS

De Petz, A; Aseptic Technic of Stomach Resections; 86 Annals of Surgery 388; Sep. 1927; 5 pages.
(Continued)

*Primary Examiner* — Eyamindae C Jallow
(74) *Attorney, Agent, or Firm* — Ulmer & Berne LLP

(57) ABSTRACT

A system for preventing unwanted tissue migration in surgical staplers includes a surgical stapler having an end effector including an upper jaw and a lower jaw. A distal end of the upper jaw is connected to a distal end of the lower jaw, and a proximal end of the upper jaw is connected to a proximal end of the lower jaw. First and second tissue stops are formed on the distal and proximal ends of the lower jaw, respectively. The second tissue stop and the proximal end of the upper jaw define a no cut zone when the surgical stapler is in an open position. The surgical stapler also includes a tissue cutting device disposed within the lower jaw for resecting tissue. The system also includes a warning, blocking, impeding, or barrier forming device for preventing the unwanted migration of tissue into the no tissue zone.

25 Claims, 19 Drawing Sheets

(52) U.S. Cl.
CPC .............. *A61B 2017/07271* (2013.01); *A61B 2017/07285* (2013.01); *A61B 2090/036* (2016.02)

(56) References Cited

U.S. PATENT DOCUMENTS

| | | | |
|---|---|---|---|
| 2,659,371 A | 11/1953 | Schnee | |
| 2,686,520 A | 8/1954 | Jarvis et al. | |
| 3,017,637 A | 1/1962 | Sampson | |
| 3,490,675 A | 1/1970 | Green et al. | |
| 3,551,987 A | 1/1971 | Wilkinson | |
| 3,877,434 A | 4/1975 | Ferguson | |
| 4,216,891 A | 8/1980 | Behlke | |
| 4,269,190 A | 5/1981 | Behney | |
| 4,319,576 A | 3/1982 | Rothfuss | |
| 4,354,628 A | 10/1982 | Green | |
| 4,442,964 A | 4/1984 | Becht | |
| 4,458,681 A | 7/1984 | Hopkins | |
| 4,494,057 A | 1/1985 | Hotta | |
| 4,520,817 A | 6/1985 | Green | |
| 4,527,724 A | 7/1985 | Chow et al. | |
| 4,558,699 A | 12/1985 | Bashour | |
| 4,605,001 A | 8/1986 | Rothfuss et al. | |
| 4,605,004 A | 8/1986 | Di Giovanni et al. | |
| 4,608,981 A | 9/1986 | Rothfuss et al. | |
| 4,610,383 A | 9/1986 | Rothfuss et al. | |
| 4,632,290 A | 12/1986 | Green et al. | |
| 4,633,861 A | 1/1987 | Chow et al. | |
| 4,676,774 A | 6/1987 | Semm et al. | |
| 4,679,557 A | 7/1987 | Opie et al. | |
| 4,705,038 A | 11/1987 | Sjostrom et al. | |
| 4,784,137 A | 11/1988 | Kulik et al. | |
| 4,803,985 A | 2/1989 | Hill | |
| 4,819,853 A | 4/1989 | Green | |
| 4,848,637 A | 7/1989 | Pruitt | |
| 4,930,503 A | 6/1990 | Pruitt | |
| 4,941,623 A | 7/1990 | Pruitt | |
| 4,951,861 A | 8/1990 | Schulze et al. | |
| 4,976,721 A | 12/1990 | Blasnik et al. | |
| 4,978,049 A | 12/1990 | Green | |
| 5,040,715 A | 8/1991 | Green et al. | |
| 5,136,220 A | 8/1992 | Philipp | |
| 5,152,744 A | 10/1992 | Krause et al. | |
| 5,176,651 A | 1/1993 | Allgood et al. | |
| 5,205,459 A | 4/1993 | Brinkerhoff et al. | |
| 5,219,111 A | 6/1993 | Bilotti et al. | |
| 5,221,036 A | 6/1993 | Takase | |
| 5,222,961 A | 6/1993 | Nakao et al. | |
| 5,258,009 A | 11/1993 | Conners | |
| 5,295,977 A | 3/1994 | Cohen et al. | |
| 5,307,976 A | 5/1994 | Cook et al. | |
| 5,308,576 A | 5/1994 | Green et al. | |
| 5,312,410 A | 5/1994 | Miller et al. | |
| 5,327,914 A | 7/1994 | Shlain | |
| 5,333,772 A | 8/1994 | Rothfuss et al. | |
| 5,345,949 A | 9/1994 | Shlain | |
| 5,389,098 A | 2/1995 | Shuichi et al. | |
| 5,395,030 A | 3/1995 | Kuramoto et al. | |
| 5,395,034 A | 3/1995 | Allen et al. | |
| 5,413,267 A | 5/1995 | Solyntjes et al. | |
| 5,415,334 A | 5/1995 | Williamson et al. | |
| 5,431,323 A | 7/1995 | Smith et al. | |
| 5,443,475 A | 8/1995 | Auerbach et al. | |
| 5,452,836 A | 9/1995 | Huitema et al. | |
| 5,452,837 A | 9/1995 | Williamson, IV et al. | |
| 5,456,401 A | 10/1995 | Green et al. | |
| 5,465,895 A | 11/1995 | Knodel et al. | |
| 5,465,896 A | 11/1995 | Mien et al. | |
| 5,469,840 A | 11/1995 | Tanii et al. | |
| 5,470,006 A | 11/1995 | Rodak | |
| 5,470,009 A | 11/1995 | Rodak | |
| 5,480,089 A | 1/1996 | Blewett | |
| 5,485,952 A | 1/1996 | Fontayne | |
| 5,487,500 A | 1/1996 | Knodel et al. | |
| 5,496,333 A | 3/1996 | Sackier et al. | |
| 5,503,638 A | 4/1996 | Cooper et al. | |
| 5,507,426 A | 4/1996 | Young et al. | |
| 5,507,773 A | 4/1996 | Huitema et al. | |
| 5,514,098 A | 5/1996 | Pfoslgraf et al. | |
| 5,531,744 A | 7/1996 | Nardella et al. | |
| 5,549,621 A | 8/1996 | Bessler et al. | |
| 5,551,622 A | 9/1996 | Yoon | |
| 5,554,169 A | 9/1996 | Green et al. | |
| 5,560,530 A | 10/1996 | Bolanos et al. | |
| 5,562,702 A | 10/1996 | Huitema et al. | |
| 5,571,116 A | 11/1996 | Bolanos et al. | |
| 5,571,131 A | 11/1996 | Ek et al. | |
| 5,586,711 A | 12/1996 | Plyley et al. | |
| 5,597,107 A | 1/1997 | Knodel et al. | |
| 5,630,540 A | 5/1997 | Blewett | |
| 5,632,432 A | 5/1997 | Schulze et al. | |
| 5,636,780 A | 6/1997 | Green et al. | |
| 5,662,667 A | 9/1997 | Knodel | |
| 5,676,674 A | 10/1997 | Bolanos et al. | |
| 5,689,159 A | 11/1997 | Culp et al. | |
| 5,697,542 A | 12/1997 | Knodel et al. | |
| 5,702,409 A | 12/1997 | Rayburn et al. | |
| 5,704,534 A | 1/1998 | Huitema et al. | |
| 5,732,871 A | 3/1998 | Clark et al. | |
| 5,762,256 A | 6/1998 | Mastri et al. | |
| 5,779,130 A | 7/1998 | Alesi et al. | |
| 5,779,132 A | 7/1998 | Knodel et al. | |
| 5,782,396 A | 7/1998 | Mastri et al. | |
| 5,797,538 A | 8/1998 | Heaton et al. | |
| 5,810,240 A | 9/1998 | Robertson | |
| 5,814,055 A | 9/1998 | Knodel et al. | |
| 5,819,240 A | 10/1998 | Kara | |
| 5,820,009 A | 10/1998 | Melling et al. | |
| 5,865,361 A | 2/1999 | Milliman et al. | |
| 5,868,760 A | 2/1999 | Mcguckin, Jr. | |
| 5,871,135 A | 2/1999 | Williamson IV et al. | |
| 5,901,895 A | 5/1999 | Heaton et al. | |
| 5,902,312 A | 5/1999 | Frater et al. | |
| 5,954,259 A | 9/1999 | Viola et al. | |
| 5,964,394 A | 10/1999 | Robertson | |
| 5,980,248 A | 11/1999 | Kusakabe et al. | |
| 5,988,479 A | 11/1999 | Palmer | |
| 6,032,849 A | 3/2000 | Mastri et al. | |
| 6,048,330 A | 4/2000 | Anthony | |
| 6,099,551 A | 8/2000 | Gabbay | |
| 6,264,087 B1 | 7/2001 | Whitman | |
| 6,270,507 B1 | 8/2001 | Callicrate | |
| 6,315,184 B1 | 11/2001 | Whitman | |
| 6,325,810 B1 | 12/2001 | Hamilton et al. | |
| 6,439,541 B1 | 8/2002 | Nsel et al. | |
| 6,488,196 B1 | 12/2002 | Fenton | |
| 6,505,768 B2 | 1/2003 | Whitman | |
| 6,511,490 B2 | 1/2003 | Robert | |
| 6,616,446 B1 | 9/2003 | Schmid | |
| 6,716,233 B1 | 4/2004 | Whitman | |
| 6,793,652 B1 | 9/2004 | Whitman et al. | |
| 6,835,199 B2 | 12/2004 | Mcguckin et al. | |
| RE38,708 E | 3/2005 | Bolanos et al. | |
| 6,953,138 B1 | 10/2005 | Dworak et al. | |
| 6,978,921 B2 | 12/2005 | Shelton, IV et al. | |
| 6,986,451 B1 | 1/2006 | Mastri et al. | |
| 6,988,649 B2 | 1/2006 | Shelton, IV et al. | |
| 7,025,791 B2 | 4/2006 | Levine et al. | |
| 7,032,799 B2 | 4/2006 | Viola et al. | |
| 7,037,344 B2 | 5/2006 | Kagan et al. | |
| 7,044,353 B2 | 5/2006 | Mastri et al. | |
| 7,070,083 B2 | 7/2006 | Jankowski | |
| 7,128,253 B2 | 10/2006 | Mastri et al. | |
| 7,134,587 B2 | 11/2006 | Schwemberger et al. | |
| 7,175,648 B2 | 2/2007 | Nakao | |
| 7,207,472 B2 | 4/2007 | Wukusick et al. | |
| 7,225,964 B2 | 6/2007 | Mastri et al. | |
| 7,229,428 B2 | 6/2007 | Gannoe et al. | |
| 7,235,089 B1 | 6/2007 | Mcguckin, Jr. | |
| 7,258,262 B2 | 8/2007 | Mastri et al. | |
| 7,278,562 B2 | 10/2007 | Mastri et al. | |
| 7,278,563 B1 | 10/2007 | Green | |
| 7,288,100 B2 | 10/2007 | Molina Trigueros | |
| 7,308,998 B2 | 12/2007 | Mastri et al. | |

(56) References Cited

U.S. PATENT DOCUMENTS

| | | | |
|---|---|---|---|
| RE40,237 E | 4/2008 | Bilotti et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,076 B2 | 8/2008 | Racenet et al. |
| 7,422,138 B2 | 9/2008 | Bilotti et al. |
| 7,434,716 B2 | 10/2008 | Viola |
| 7,434,717 B2 | 10/2008 | Shelton, IV et al. |
| 7,438,209 B1 | 10/2008 | Hess et al. |
| 7,455,676 B2 | 11/2008 | Holsten et al. |
| 7,467,740 B2 | 12/2008 | Shelton, IV et al. |
| 7,472,815 B2 | 1/2009 | Shelton, IV et al. |
| 7,481,349 B2 | 1/2009 | Holsten et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,564 B2 | 6/2009 | Boudreaux |
| 7,549,654 B2 | 6/2009 | Anderson et al. |
| 7,565,993 B2 | 7/2009 | Milliman et al. |
| 7,588,175 B2 | 9/2009 | Timm et al. |
| 7,588,176 B2 | 9/2009 | Timm et al. |
| 7,588,177 B2 | 9/2009 | Racenet |
| 7,604,151 B2 | 10/2009 | Hess et al. |
| 7,617,961 B2 | 11/2009 | Viola |
| 7,635,074 B2 | 12/2009 | Olson et al. |
| 7,641,091 B2 | 1/2010 | Olson et al. |
| 7,645,285 B2 | 1/2010 | Cosgrove et al. |
| 7,658,312 B2 | 2/2010 | Vidal et al. |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,673,781 B2 | 3/2010 | Swayze et al. |
| 7,673,782 B2 | 3/2010 | Hess et al. |
| 7,690,547 B2 | 4/2010 | Racenet et al. |
| 7,694,864 B2 | 4/2010 | Okada et al. |
| 7,704,264 B2 | 4/2010 | Ewers et al. |
| 7,708,684 B2 | 5/2010 | Demarais et al. |
| 7,717,312 B2 | 5/2010 | Beetel |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,744,613 B2 | 6/2010 | Ewers et al. |
| 7,758,493 B2 | 7/2010 | Gingras |
| 7,770,774 B2 | 8/2010 | Mastri et al. |
| 7,775,967 B2 | 8/2010 | Gertner |
| D624,182 S | 9/2010 | Thouement |
| 7,793,812 B2 | 9/2010 | Moore et al. |
| 7,794,475 B2 | 9/2010 | Hess et al. |
| 7,815,092 B2 | 10/2010 | Whitman et al. |
| 7,819,896 B2 | 10/2010 | Racenet |
| 7,828,188 B2 | 11/2010 | Jankowski |
| 7,837,079 B2 | 11/2010 | Holsten et al. |
| 7,846,149 B2 | 12/2010 | Jankowski |
| 7,857,184 B2 | 12/2010 | Viola |
| 7,866,525 B2 | 1/2011 | Scirica |
| 7,866,528 B2 | 1/2011 | Olson et al. |
| 7,871,416 B2 | 1/2011 | Phillips |
| 7,891,531 B1 | 2/2011 | Ward |
| 7,891,533 B2 | 2/2011 | Green et al. |
| 7,913,893 B2 | 3/2011 | Mastri et al. |
| 7,918,869 B2 | 4/2011 | Saadat et al. |
| 7,934,630 B2 | 5/2011 | Shelton, IV et al. |
| 7,955,340 B2 | 6/2011 | Michlitsch et al. |
| 7,959,050 B2 | 6/2011 | Smith et al. |
| 7,963,907 B2 | 6/2011 | Gertner |
| 7,966,799 B2 | 6/2011 | Morgan et al. |
| 7,992,757 B2 | 8/2011 | Wheeler et al. |
| 7,997,469 B2 | 8/2011 | Olson et al. |
| 8,016,176 B2 | 9/2011 | Kasvikis et al. |
| 8,020,741 B2 | 9/2011 | Cole et al. |
| 8,028,884 B2 | 10/2011 | Sniffin et al. |
| 8,033,442 B2 | 10/2011 | Racenet et al. |
| 8,034,077 B2 | 10/2011 | Smith et al. |
| 8,052,697 B2 | 11/2011 | Phillips |
| 8,056,788 B2 | 11/2011 | Mastri et al. |
| 8,061,577 B2 | 11/2011 | Racenet et al. |
| 8,062,236 B2 | 11/2011 | Soltz |
| 8,066,168 B2 | 11/2011 | Vidal et al. |
| 8,070,034 B1 | 12/2011 | Knodel |
| 8,070,036 B1 | 12/2011 | Knodel |
| 8,087,563 B2 | 1/2012 | Milliman et al. |
| 8,091,756 B2 | 1/2012 | Viola |
| 8,096,459 B2 | 1/2012 | Ortiz et al. |
| 8,113,406 B2 | 2/2012 | Holsten et al. |
| 8,132,704 B2 | 3/2012 | Whitman et al. |
| 8,141,762 B2 | 3/2012 | Bedi et al. |
| 8,147,506 B2 | 4/2012 | Ortiz et al. |
| 8,167,186 B2 | 5/2012 | Racenet et al. |
| 8,172,122 B2 | 5/2012 | Kasvikis et al. |
| 8,186,560 B2 | 5/2012 | Hess et al. |
| 8,196,795 B2 | 6/2012 | Moore et al. |
| 8,205,780 B2 | 6/2012 | Sorrentino et al. |
| 8,210,415 B2 | 7/2012 | Ward |
| 8,216,159 B1 | 7/2012 | Leiboff |
| 8,220,690 B2 | 7/2012 | Hess et al. |
| 8,226,602 B2 | 7/2012 | Quijano et al. |
| 8,245,898 B2 | 8/2012 | Smith et al. |
| 8,252,009 B2 | 8/2012 | Weller et al. |
| 8,256,655 B2 | 9/2012 | Sniffin et al. |
| 8,276,801 B2 | 10/2012 | Zemlok et al. |
| 8,292,153 B2 | 10/2012 | Jankowski |
| 8,308,725 B2 | 11/2012 | Bell et al. |
| 8,317,070 B2 | 11/2012 | Hueil et al. |
| 8,322,455 B2 | 12/2012 | Shelton, IV et al. |
| 8,328,061 B2 | 12/2012 | Kasvikis |
| 8,328,064 B2 | 12/2012 | Racenet et al. |
| 8,343,175 B2 | 1/2013 | Ewers et al. |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,436 B2 | 1/2013 | Kasvikis |
| 8,360,297 B2 | 1/2013 | Shelton, IV et al. |
| 8,360,298 B2 * | 1/2013 | Farascioni ....... A61B 17/07207 227/176.1 |
| 8,365,973 B1 | 2/2013 | White et al. |
| 8,365,976 B2 | 2/2013 | Hess et al. |
| 8,382,775 B1 | 2/2013 | Bender et al. |
| 8,393,513 B2 | 3/2013 | Jankowski |
| 8,393,514 B2 | 3/2013 | Shelton, IV et al. |
| 8,403,956 B1 | 3/2013 | Thompson et al. |
| 8,408,442 B2 | 4/2013 | Racenet et al. |
| 8,424,739 B2 | 4/2013 | Racenet et al. |
| 8,439,244 B2 | 5/2013 | Holcomb et al. |
| 8,439,246 B1 | 5/2013 | Knodel |
| 8,449,460 B2 | 5/2013 | Duke et al. |
| 8,449,560 B2 | 5/2013 | Roth et al. |
| 8,453,912 B2 | 6/2013 | Mastri et al. |
| 8,453,914 B2 | 6/2013 | Laurent et al. |
| 8,464,923 B2 | 6/2013 | Shelton, Iv |
| 8,465,507 B2 | 6/2013 | Cosgrove et al. |
| 8,469,252 B2 | 6/2013 | Holcomb et al. |
| 8,469,977 B2 | 6/2013 | Balbierz et al. |
| 8,479,969 B2 | 7/2013 | Shelton, IV |
| 8,485,412 B2 | 7/2013 | Shelton, Iv et al. |
| 8,496,155 B2 | 7/2013 | Knodel |
| 8,496,156 B2 | 7/2013 | Sniffin et al. |
| 8,499,993 B2 | 8/2013 | Shelton, IV et al. |
| 8,523,041 B2 | 9/2013 | Ishitsuki et al. |
| 8,529,585 B2 | 9/2013 | Jacobs et al. |
| 8,540,128 B2 | 9/2013 | Shelton, IV et al. |
| 8,540,130 B2 | 9/2013 | Moore et al. |
| 8,544,712 B2 | 10/2013 | Jankowski |
| 8,561,872 B2 | 10/2013 | Wheeler et al. |
| 8,573,465 B2 | 11/2013 | Shelton, IV |
| 8,574,243 B2 | 11/2013 | Saadat et al. |
| 8,579,176 B2 | 11/2013 | Smith et al. |
| 8,579,178 B2 | 11/2013 | Holsten et al. |
| 8,590,762 B2 | 11/2013 | Hess et al. |
| 8,596,513 B2 | 12/2013 | Olson et al. |
| 8,608,043 B2 | 12/2013 | Scirica |
| 8,608,046 B2 | 12/2013 | Laurent et al. |

(56) References Cited

U.S. PATENT DOCUMENTS

| | | |
|---|---|---|
| 8,613,384 B2 | 12/2013 | Pastorelli et al. |
| 8,616,431 B2 | 12/2013 | Timm et al. |
| 8,617,185 B2 | 12/2013 | Bonutti et al. |
| 8,628,544 B2 | 1/2014 | Farascioni |
| 8,628,547 B2 | 1/2014 | Weller et al. |
| 8,647,350 B2 | 2/2014 | Mohan et al. |
| 8,663,245 B2 | 3/2014 | Hobday et al. |
| 8,668,130 B2 | 3/2014 | Hess et al. |
| 8,672,208 B2 | 3/2014 | Hess et al. |
| 8,672,830 B2 | 3/2014 | Marcotte et al. |
| 8,701,958 B2 | 4/2014 | Shelton, IV et al. |
| 8,714,429 B2 | 5/2014 | Demmy |
| 8,720,766 B2 | 5/2014 | Hess et al. |
| 8,727,197 B2 | 5/2014 | Hess et al. |
| 8,727,199 B2 | 5/2014 | Wenchell |
| 8,733,613 B2 | 5/2014 | Huitema et al. |
| 8,740,035 B2 | 6/2014 | Mastri et al. |
| 8,758,392 B2 | 6/2014 | Crainich |
| 8,763,875 B2 | 7/2014 | Morgan et al. |
| 8,800,838 B2 | 8/2014 | Shelton, IVv |
| 8,800,840 B2 | 8/2014 | Jankowski |
| 8,801,732 B2 | 8/2014 | Harris et al. |
| 8,808,325 B2 | 8/2014 | Hess et al. |
| 8,840,004 B2 | 9/2014 | Holsten et al. |
| 8,852,218 B2 | 10/2014 | Hughett, Sr. et al. |
| 8,864,009 B2 | 10/2014 | Shelton, IV et al. |
| 8,899,465 B2 | 12/2014 | Shelton, Iv et al. |
| 8,925,788 B2 | 1/2015 | Hess et al. |
| 8,945,163 B2 | 2/2015 | Voegele et al. |
| 8,956,390 B2 | 2/2015 | Shah et al. |
| 8,973,804 B2 | 3/2015 | Hess et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,998,058 B2 | 4/2015 | Moore et al. |
| 9,016,541 B2 | 4/2015 | Viola et al. |
| 9,033,203 B2 | 5/2015 | Woodard, Jr. et al. |
| 9,066,721 B2 | 6/2015 | Ichihara et al. |
| 9,084,600 B1 | 7/2015 | Knodel et al. |
| 9,084,601 B2 | 7/2015 | Moore et al. |
| 9,095,339 B2 | 8/2015 | Moore et al. |
| 9,113,862 B2 | 8/2015 | Morgan et al. |
| 9,113,868 B2 | 8/2015 | Felder et al. |
| 9,119,627 B2 | 9/2015 | Cosgrove et al. |
| 9,138,226 B2 | 9/2015 | Racenet et al. |
| 9,149,325 B2 | 10/2015 | Worrell et al. |
| 9,155,528 B2 | 10/2015 | Bender et al. |
| 9,168,039 B1 | 10/2015 | Knodel |
| 9,179,911 B2 | 11/2015 | Morgan et al. |
| 9,180,035 B2 | 11/2015 | Stack et al. |
| 9,216,019 B2 | 12/2015 | Schmid et al. |
| 9,254,131 B2 | 2/2016 | Soltz et al. |
| 9,289,206 B2 | 3/2016 | Hess et al. |
| 9,289,207 B2 | 3/2016 | Shelton, IV |
| 9,307,981 B2 | 4/2016 | Mikkaichi et al. |
| 9,314,362 B2 | 4/2016 | Bender et al. |
| 9,326,768 B2 | 5/2016 | Shelton, IV |
| 9,339,442 B2 | 5/2016 | Tai et al. |
| 9,345,478 B2 | 5/2016 | Knodel |
| 9,364,225 B2 | 6/2016 | Sniffin et al. |
| 9,370,362 B2 | 6/2016 | Petty et al. |
| 9,398,917 B2 | 7/2016 | Whitfield et al. |
| 9,408,604 B2 | 8/2016 | Shelton, IV et al. |
| 9,433,411 B2 | 9/2016 | Racenet et al. |
| 9,439,633 B2 | 9/2016 | O'Dea |
| 9,498,219 B2 | 11/2016 | Moore et al. |
| 9,549,733 B2 | 1/2017 | Knodel |
| 9,561,032 B2 | 2/2017 | Shelton, IV et al. |
| 9,603,595 B2 | 3/2017 | Shelton, IV et al. |
| 9,603,598 B2 | 3/2017 | Shelton, IV et al. |
| 9,615,952 B2 | 4/2017 | Scott et al. |
| 9,636,114 B2 | 5/2017 | Cole et al. |
| 9,675,355 B2 | 6/2017 | Shelton, IV et al. |
| 9,687,233 B2 | 6/2017 | Fernandez et al. |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,724,093 B2 | 8/2017 | Farascioni et al. |
| 9,724,096 B2 | 8/2017 | Thompson et al. |
| 9,730,692 B2 | 8/2017 | Shelton, IV et al. |
| 9,775,613 B2 | 10/2017 | Shelton, IV et al. |
| 9,801,627 B2 | 10/2017 | Harris et al. |
| 9,801,628 B2 | 10/2017 | Harris et al. |
| 9,801,630 B2 | 10/2017 | Harris et al. |
| 9,808,246 B2 | 11/2017 | Shelton, IV et al. |
| 9,808,257 B2 | 11/2017 | Armenteros et al. |
| 9,820,742 B2 | 11/2017 | Covach et al. |
| 9,827,002 B2 | 11/2017 | Hausen et al. |
| 9,844,370 B2 | 12/2017 | Viola et al. |
| 9,848,873 B2 | 12/2017 | Shelton, IV |
| 9,848,875 B2 | 12/2017 | Aronhalt et al. |
| 9,848,878 B2 | 12/2017 | Racenet et al. |
| 9,855,040 B2 | 1/2018 | Kostrzewski |
| 9,861,366 B2 | 1/2018 | Aranyi |
| 9,872,682 B2 | 1/2018 | Hess et al. |
| 9,901,344 B2 | 2/2018 | Moore et al. |
| 9,901,346 B2 | 2/2018 | Moore et al. |
| 9,913,646 B2 | 3/2018 | Shelton, IV |
| 9,924,947 B2 | 3/2018 | Shelton, IV et al. |
| 9,936,953 B2 * | 4/2018 | Thompson .......... A61B 17/3468 |
| 9,980,729 B2 | 5/2018 | Moore et al. |
| 9,999,426 B2 | 6/2018 | Moore et al. |
| 9,999,431 B2 | 6/2018 | Shelton, IV et al. |
| 10,004,505 B2 | 6/2018 | Moore et al. |
| 10,045,780 B2 | 8/2018 | Adams et al. |
| 10,085,754 B2 | 10/2018 | Sniffin et al. |
| 10,130,360 B2 | 11/2018 | Olson et al. |
| 10,130,363 B2 | 11/2018 | Huitema et al. |
| 10,172,616 B2 | 1/2019 | Murray et al. |
| 10,194,912 B2 | 2/2019 | Scheib et al. |
| 10,226,250 B2 | 3/2019 | Beckman et al. |
| 10,231,734 B2 | 3/2019 | Thompson et al. |
| 10,238,517 B2 | 3/2019 | Gingras |
| 10,245,032 B2 | 4/2019 | Shelton, IV |
| 10,258,334 B2 | 4/2019 | Adams et al. |
| 10,265,073 B2 | 4/2019 | Scheib et al. |
| 10,278,695 B2 | 5/2019 | Milo |
| 10,278,699 B2 | 5/2019 | Thompson et al. |
| 10,278,707 B2 | 5/2019 | Thompson et al. |
| 10,285,712 B2 | 5/2019 | Cosgrove, III et al. |
| 10,285,837 B1 | 5/2019 | Thompson et al. |
| 10,292,706 B2 | 5/2019 | Jankowski |
| 10,307,161 B2 | 6/2019 | Jankowski |
| 10,307,163 B2 | 6/2019 | Moore et al. |
| 10,314,580 B2 | 6/2019 | Scheib et al. |
| 10,314,589 B2 | 6/2019 | Shelton, IV et al. |
| 10,342,538 B2 | 7/2019 | Racenet et al. |
| 10,383,628 B2 | 8/2019 | Kang et al. |
| 10,390,826 B2 | 8/2019 | Badawi |
| 10,405,856 B2 | 9/2019 | Knodel |
| 10,405,860 B2 | 9/2019 | Thompson et al. |
| 10,420,559 B2 | 9/2019 | Marczyk et al. |
| 10,420,560 B2 | 9/2019 | Shelton, IV et al. |
| 10,441,283 B1 | 10/2019 | Thompson et al. |
| 10,456,571 B2 | 10/2019 | Cairns |
| 10,470,911 B2 | 11/2019 | Thompson et al. |
| 10,499,912 B2 | 12/2019 | Scheib et al. |
| 10,537,325 B2 | 1/2020 | Bakos et al. |
| 10,542,986 B2 | 1/2020 | Thompson et al. |
| 10,548,597 B2 | 2/2020 | Dunki-Jacobs et al. |
| 10,610,226 B2 | 4/2020 | Shelton et al. |
| 10,624,638 B2 | 4/2020 | Thompson et al. |
| 10,687,807 B2 | 6/2020 | Simms et al. |
| 10,687,810 B2 | 6/2020 | Shelton, IV et al. |
| 10,687,814 B2 | 6/2020 | Dunki-Jacobs et al. |
| 10,716,564 B2 | 7/2020 | Shelton, IV et al. |
| 10,758,231 B2 | 9/2020 | Harris et al. |
| 10,849,623 B2 | 12/2020 | Dunki-Jacobs et al. |
| 10,912,562 B2 | 2/2021 | Dunki-Jacobs et al. |
| 10,966,717 B2 * | 4/2021 | Shah .................. A61B 17/1285 |
| 10,966,721 B2 | 4/2021 | Dunki-Jacobs et al. |
| 10,987,108 B2 | 4/2021 | Thompson et al. |
| 11,173,060 B2 * | 11/2021 | Thompson ............. A61F 5/005 |
| 2001/0044656 A1 | 11/2001 | Williamson, IV et al. |

(56) References Cited

U.S. PATENT DOCUMENTS

| | | |
|---|---|---|
| 2002/0143346 A1 | 10/2002 | Mcguckin, Jr. et al. |
| 2003/0125734 A1 | 7/2003 | Mollenauer |
| 2003/0135091 A1 | 7/2003 | Nakazawa et al. |
| 2003/0220660 A1 | 11/2003 | Kortenbach et al. |
| 2004/0006351 A1 | 1/2004 | Gannoe et al. |
| 2004/0006372 A1 | 1/2004 | Racenet et al. |
| 2004/0068267 A1 | 4/2004 | Harvie et al. |
| 2004/0181239 A1 | 9/2004 | Dorn et al. |
| 2005/0006432 A1 | 1/2005 | Racenet et al. |
| 2005/0080444 A1 | 4/2005 | Kraemer et al. |
| 2005/0139633 A1 | 6/2005 | Wukusick et al. |
| 2005/0203547 A1 | 9/2005 | Weller et al. |
| 2006/0011698 A1 | 1/2006 | Okada et al. |
| 2006/0016853 A1 | 1/2006 | Racenet |
| 2006/0020277 A1 | 1/2006 | Gostout et al. |
| 2006/0036267 A1 | 2/2006 | Saadat et al. |
| 2006/0041270 A1 | 2/2006 | Lenker et al. |
| 2006/0085030 A1 | 4/2006 | Bettuchi et al. |
| 2006/0151568 A1 | 7/2006 | Weller et al. |
| 2006/0229665 A1 | 10/2006 | Wales et al. |
| 2006/0241692 A1 | 10/2006 | Mcguckin et al. |
| 2007/0023477 A1 | 2/2007 | Whitman et al. |
| 2007/0027469 A1 | 2/2007 | Smith et al. |
| 2007/0029364 A1 | 2/2007 | Kruszynski et al. |
| 2007/0034666 A1 | 2/2007 | Holsten et al. |
| 2007/0034667 A1 | 2/2007 | Holsten et al. |
| 2007/0039997 A1 | 2/2007 | Mather et al. |
| 2007/0056932 A1 | 3/2007 | Whitman et al. |
| 2007/0075114 A1 | 4/2007 | Shelton et al. |
| 2007/0083233 A1 | 4/2007 | Ortiz et al. |
| 2007/0131732 A1 | 6/2007 | Holsten et al. |
| 2007/0179528 A1 | 8/2007 | Soltz et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0213743 A1 | 9/2007 | Mcguckin, Jr. |
| 2007/0246505 A1 | 10/2007 | Pace-Floridia et al. |
| 2007/0262116 A1 | 11/2007 | Hueil et al. |
| 2008/0015631 A1 | 1/2008 | Lee et al. |
| 2008/0023522 A1 | 1/2008 | Olson et al. |
| 2008/0033457 A1 | 2/2008 | Hobday et al. |
| 2008/0035702 A1 | 2/2008 | Holsten et al. |
| 2008/0041918 A1 | 2/2008 | Holsten et al. |
| 2008/0058716 A1 | 3/2008 | Dubrul et al. |
| 2008/0078800 A1 | 4/2008 | Hess et al. |
| 2008/0082124 A1 | 4/2008 | Hess et al. |
| 2008/0087707 A1 | 4/2008 | Jankowski |
| 2008/0097332 A1 | 4/2008 | Greenhalgh et al. |
| 2008/0149684 A1 | 6/2008 | Viola |
| 2008/0164297 A1 | 7/2008 | Holsten et al. |
| 2008/0169329 A1 | 7/2008 | Shelton et al. |
| 2008/0169332 A1 | 7/2008 | Shelton et al. |
| 2008/0190990 A1 | 8/2008 | Holsten et al. |
| 2008/0203134 A1 | 8/2008 | Shah et al. |
| 2008/0249404 A1 | 10/2008 | Mikkaichi et al. |
| 2008/0275480 A1 | 11/2008 | Jacobs et al. |
| 2008/0294179 A1 | 11/2008 | Balbierz et al. |
| 2008/0308602 A1 | 12/2008 | Fimm et al. |
| 2009/0001122 A1 | 1/2009 | Prommersberger et al. |
| 2009/0001130 A1 | 1/2009 | Hess et al. |
| 2009/0012556 A1 | 1/2009 | Boudreaux et al. |
| 2009/0020584 A1 | 1/2009 | Soltz et al. |
| 2009/0078739 A1 | 3/2009 | Viola |
| 2009/0134200 A1 | 5/2009 | Farinelli et al. |
| 2009/0173766 A1 | 7/2009 | Wenchell |
| 2009/0209946 A1 | 8/2009 | Kolata et al. |
| 2009/0209986 A1 | 8/2009 | Stewart et al. |
| 2009/0212088 A1 | 8/2009 | Okada et al. |
| 2009/0255974 A1 | 10/2009 | Viola |
| 2009/0261144 A1 | 10/2009 | Sniffin et al. |
| 2009/0308907 A1 | 12/2009 | Nalagatla et al. |
| 2010/0010512 A1 | 1/2010 | Taylor et al. |
| 2010/0072255 A1 | 3/2010 | Olson et al. |
| 2010/0072258 A1 | 3/2010 | Farascioni et al. |
| 2010/0108739 A1 | 5/2010 | Holsten et al. |
| 2010/0114124 A1 | 5/2010 | Kelleher et al. |
| 2010/0121356 A1 | 5/2010 | Hartmann et al. |
| 2010/0137904 A1 | 6/2010 | Wenchell |
| 2010/0145324 A1 | 6/2010 | Nihalani |
| 2010/0213240 A1 | 8/2010 | Kostrzewski |
| 2010/0256634 A1 | 10/2010 | Voegele et al. |
| 2010/0282820 A1 | 11/2010 | Kasvikis |
| 2010/0331866 A1 | 12/2010 | Surti et al. |
| 2011/0004062 A1 | 1/2011 | Asai et al. |
| 2011/0017800 A1 | 1/2011 | Viola |
| 2011/0046653 A1 | 2/2011 | Addington et al. |
| 2011/0071555 A1 | 3/2011 | Mcbrayer et al. |
| 2011/0084113 A1 | 4/2011 | Bedi et al. |
| 2011/0087169 A1 | 4/2011 | Parihar et al. |
| 2011/0087259 A1* | 4/2011 | Marczyk ............ A61B 17/072 606/170 |
| 2011/0087279 A1 | 4/2011 | Shah et al. |
| 2011/0152895 A1 | 6/2011 | Nyuli et al. |
| 2011/0160752 A1 | 6/2011 | Aguirre |
| 2011/0178454 A1 | 7/2011 | Gagner et al. |
| 2011/0186614 A1 | 8/2011 | Kasvikis |
| 2011/0190791 A1 | 8/2011 | Jacobs et al. |
| 2011/0208211 A1 | 8/2011 | Whitfield et al. |
| 2011/0226837 A1 | 9/2011 | Baxter, III et al. |
| 2011/0278343 A1 | 11/2011 | Knodel et al. |
| 2011/0290851 A1 | 12/2011 | Shelton, IV |
| 2011/0315739 A1 | 12/2011 | Sniffin et al. |
| 2012/0059400 A1 | 3/2012 | Williamson, IV et al. |
| 2012/0080473 A1* | 4/2012 | Farascioni ........... A61B 17/068 227/175.1 |
| 2012/0080494 A1 | 4/2012 | Thompson et al. |
| 2012/0123463 A1 | 5/2012 | Jacobs |
| 2012/0175398 A1 | 7/2012 | Sandborn et al. |
| 2012/0203247 A1 | 8/2012 | Shelton, IV et al. |
| 2012/0234899 A1 | 9/2012 | Scheib et al. |
| 2012/0234900 A1 | 9/2012 | Swayze |
| 2012/0248169 A1 | 10/2012 | Widenhouse et al. |
| 2012/0248170 A1* | 10/2012 | Marczyk ................ A61B 90/03 227/175.1 |
| 2012/0277525 A1 | 11/2012 | O'Dea |
| 2012/0286022 A1 | 11/2012 | Olson et al. |
| 2013/0062394 A1 | 3/2013 | Smith et al. |
| 2013/0075447 A1 | 3/2013 | Setseretai. |
| 2013/0075450 A1 | 3/2013 | Schmid et al. |
| 2013/0092718 A1 | 4/2013 | Soltz et al. |
| 2013/0105549 A1 | 5/2013 | Holsten et al. |
| 2013/0131440 A1 | 5/2013 | Gabriel |
| 2013/0146638 A1 | 6/2013 | Mandakolathur Vasudevan et al. |
| 2013/0146641 A1 | 6/2013 | Shelton, IV et al. |
| 2013/0146642 A1 | 6/2013 | Shelton, IV et al. |
| 2013/0153625 A1 | 6/2013 | Felder et al. |
| 2013/0153634 A1 | 6/2013 | Carter et al. |
| 2013/0153642 A1 | 6/2013 | Felder et al. |
| 2013/0161374 A1 | 6/2013 | Swayze et al. |
| 2013/0165774 A1 | 6/2013 | Nocca |
| 2013/0172929 A1 | 7/2013 | Dunki-Jacobs et al. |
| 2013/0193190 A1 | 8/2013 | Carter et al. |
| 2013/0214025 A1 | 8/2013 | Zemlok et al. |
| 2013/0245652 A1 | 9/2013 | Cosgrove et al. |
| 2013/0256372 A1 | 10/2013 | Baxter, III et al. |
| 2013/0256375 A1 | 10/2013 | Shelton, IV et al. |
| 2013/0256377 A1 | 10/2013 | Schmid et al. |
| 2013/0284791 A1 | 10/2013 | Dlson et al. |
| 2013/0306704 A1 | 11/2013 | Balbierz et al. |
| 2013/0327809 A1 | 12/2013 | Shelton, IV et al. |
| 2013/0334288 A1 | 12/2013 | Shelton, IV |
| 2013/0341374 A1 | 12/2013 | Shelton, IV et al. |
| 2014/0005678 A1 | 1/2014 | Shelton, IV et al. |
| 2014/0027493 A1 | 1/2014 | Jankowski |
| 2014/0046345 A1 | 2/2014 | Armenteros et al. |
| 2014/0074131 A1 | 3/2014 | Armenteros et al. |
| 2014/0081176 A1 | 3/2014 | Hassan |
| 2014/0082497 A1 | 3/2014 | Chalouhi et al. |
| 2014/0107698 A1 | 4/2014 | Inge |
| 2014/0110457 A1 | 4/2014 | Zhang et al. |
| 2014/0114121 A1 | 4/2014 | Trivedi |
| 2014/0131418 A1 | 5/2014 | Kostrzewski |
| 2014/0131419 A1 | 5/2014 | Bettuchi |
| 2014/0144968 A1 | 5/2014 | Shelton, IV |

(56) References Cited

U.S. PATENT DOCUMENTS

| | | |
|---|---|---|
| 2014/0148731 A1 | 5/2014 | Radl et al. |
| 2014/0171744 A1 | 6/2014 | Racenet et al. |
| 2014/0183242 A1 | 7/2014 | Farascioni et al. |
| 2014/0184519 A1 | 7/2014 | Benchenaa et al. |
| 2014/0191015 A1 | 7/2014 | Shelton, IV |
| 2014/0214025 A1 | 7/2014 | Worrell et al. |
| 2014/0231489 A1 | 8/2014 | Balbierz et al. |
| 2014/0239037 A1 | 8/2014 | Boudreaux et al. |
| 2014/0257353 A1 | 9/2014 | Whitman et al. |
| 2014/0263570 A1 | 9/2014 | Hopkins et al. |
| 2014/0276932 A1 | 9/2014 | Williams et al. |
| 2014/0291379 A1 | 10/2014 | Schellin et al. |
| 2015/0048141 A1 | 2/2015 | Felder et al. |
| 2015/0083780 A1 | 3/2015 | Shelton, IV et al. |
| 2015/0133740 A1 | 5/2015 | Dierking et al. |
| 2015/0157318 A1 | 6/2015 | Beardsley et al. |
| 2015/0173755 A1 | 6/2015 | Baxter, III et al. |
| 2015/0173762 A1 | 6/2015 | Shelton, IV et al. |
| 2015/0209034 A1 | 7/2015 | Viola et al. |
| 2015/0265276 A1 | 9/2015 | Huitema et al. |
| 2015/0297224 A1 | 10/2015 | Bruewer et al. |
| 2015/0297227 A1 | 10/2015 | Huitema et al. |
| 2015/0320423 A1 | 11/2015 | Aranyi |
| 2015/0351764 A1 | 12/2015 | Shelton, IV |
| 2016/0058447 A1 | 3/2016 | Posada et al. |
| 2016/0058594 A1 | 3/2016 | Armenteros et al. |
| 2016/0066916 A1 | 3/2016 | Overmyer et al. |
| 2016/0067074 A1 | 3/2016 | Thompson et al. |
| 2016/0089148 A1 | 3/2016 | Harris et al. |
| 2016/0166256 A1 | 6/2016 | Baxter, III et al. |
| 2016/0183945 A1 | 6/2016 | Shelton, IV et al. |
| 2016/0199061 A1 | 7/2016 | Shelton, IV et al. |
| 2016/0199088 A1 | 7/2016 | Shelton, IV et al. |
| 2016/0213302 A1 | 7/2016 | Frushour |
| 2016/0235409 A1 | 8/2016 | Shelton, IV et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242783 A1 | 8/2016 | Shelton, IV et al. |
| 2016/0262744 A1 | 9/2016 | Milo et al. |
| 2016/0262750 A1* | 9/2016 | Hausen .................. A61B 17/32 |
| 2016/0262921 A1 | 9/2016 | Balbierz et al. |
| 2016/0270792 A1 | 9/2016 | Sniffin et al. |
| 2016/0324527 A1* | 11/2016 | Thompson ............ A61B 17/122 |
| 2016/0354085 A1 | 12/2016 | Shelton, IV et al. |
| 2016/0367250 A1 | 12/2016 | Racenet et al. |
| 2017/0007248 A1 | 1/2017 | Shelton, IV et al. |
| 2017/0014125 A1 | 1/2017 | Shelton, IV et al. |
| 2017/0055991 A1 | 3/2017 | Kang |
| 2017/0086847 A1 | 3/2017 | Dinardo et al. |
| 2017/0095251 A1* | 4/2017 | Thompson ......... A61B 17/3468 |
| 2017/0105728 A1 | 4/2017 | Scheib et al. |
| 2017/0172571 A1* | 6/2017 | Thompson ....... A61B 17/07207 |
| 2017/0231633 A1 | 8/2017 | Marczyk et al. |
| 2017/0290588 A1 | 10/2017 | Thompson et al. |
| 2017/0303952 A1 | 10/2017 | Nativ et al. |
| 2017/0319210 A1 | 11/2017 | Moore et al. |
| 2017/0333041 A1 | 11/2017 | Moore et al. |
| 2017/0360447 A1 | 12/2017 | Armenteros et al. |
| 2017/0367697 A1 | 12/2017 | Shelton, IV et al. |
| 2018/0014826 A1 | 1/2018 | Scheib et al. |
| 2018/0036000 A1 | 2/2018 | Terada et al. |
| 2018/0036005 A1 | 2/2018 | Covach et al. |
| 2018/0092641 A1 | 4/2018 | Aranyi |
| 2018/0168620 A1 | 6/2018 | Huang et al. |
| 2018/0168633 A1 | 6/2018 | Shelton, IV et al. |
| 2018/0199939 A1 | 7/2018 | Thompson et al. |
| 2018/0199941 A1 | 7/2018 | Thompson et al. |
| 2018/0235625 A1 | 8/2018 | Shelton, IV et al. |
| 2018/0235626 A1 | 8/2018 | Shelton, IV et al. |
| 2018/0280020 A1 | 10/2018 | Hess et al. |
| 2018/0317905 A1 | 11/2018 | Olson et al. |
| 2019/0000455 A1 | 1/2019 | Adams et al. |
| 2019/0046186 A1 | 2/2019 | Dunki-Jacobs et al. |
| 2019/0046189 A1* | 2/2019 | Dunki-Jacobs .... A61B 17/0686 |
| 2019/0046190 A1 | 2/2019 | Dunki-Jacobs et al. |
| 2019/0046191 A1 | 2/2019 | Dunki-Jacobs et al. |
| 2019/0046192 A1 | 2/2019 | Dunki-Jacobs et al. |
| 2019/0046193 A1 | 2/2019 | Dunki-Jacobs et al. |
| 2019/0105042 A1 | 4/2019 | Huitema et al. |
| 2019/0133577 A1 | 5/2019 | Weadock et al. |
| 2019/0150924 A1 | 5/2019 | Thompson et al. |
| 2019/0209173 A1 | 7/2019 | Thompson et al. |
| 2019/0209175 A1 | 7/2019 | Thompson et al. |
| 2019/0224029 A1 | 7/2019 | Thompson et al. |
| 2019/0261985 A1 | 8/2019 | Adams et al. |
| 2019/0261991 A1 | 8/2019 | Beckman et al. |
| 2019/0269408 A1 | 9/2019 | Jankowski |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0307450 A1 | 10/2019 | Thompson et al. |
| 2019/0343519 A1 | 11/2019 | Thompson et al. |
| 2019/0380742 A1 | 12/2019 | Hall et al. |
| 2019/0388092 A1 | 12/2019 | Thompson et al. |
| 2020/0008964 A1 | 1/2020 | Thompson et al. |
| 2020/0015822 A1 | 1/2020 | Marczyk et al. |
| 2020/0054326 A1 | 2/2020 | Harris et al. |
| 2020/0100790 A1 | 4/2020 | Dinardo et al. |
| 2020/0205810 A1 | 7/2020 | Posey et al. |
| 2020/0205827 A1 | 7/2020 | Bakos et al. |
| 2020/0214703 A1 | 7/2020 | Thompson et al. |
| 2020/0229818 A1 | 7/2020 | Thompson et al. |
| 2020/0268385 A1 | 8/2020 | Dunki-Jacobs et al. |
| 2020/0297344 A1 | 9/2020 | Dunki-Jacobs et al. |
| 2020/0305865 A1 | 10/2020 | Shelton, IV |
| 2020/0305868 A1 | 10/2020 | Shelton, IV |
| 2020/0305869 A1 | 10/2020 | Shelton, IV |
| 2020/0305873 A1 | 10/2020 | Dunki-Jacobs et al. |
| 2020/0390443 A1 | 12/2020 | Thompson et al. |
| 2021/0128335 A1 | 5/2021 | Thompson et al. |
| 2021/0177411 A1* | 6/2021 | Williams ......... A61B 17/07207 |

FOREIGN PATENT DOCUMENTS

| | | |
|---|---|---|
| EP | 399699 A1 | 11/1990 |
| EP | 503662 A1 | 9/1992 |
| EP | 666057 A2 | 8/1995 |
| EP | 669104 A1 | 8/1995 |
| EP | 1090592 A1 | 4/2001 |
| EP | 1616526 A1 | 1/2006 |
| EP | 1769766 A1 | 4/2007 |
| EP | 1774916 A1 | 4/2007 |
| EP | 1806101 A1 | 7/2007 |
| EP | 1875868 A1 | 1/2008 |
| EP | 1875870 A1 | 1/2008 |
| EP | 1938759 A2 | 7/2008 |
| EP | 2005896 A2 | 12/2008 |
| EP | 2005897 A2 | 12/2008 |
| EP | 2005898 A2 | 12/2008 |
| EP | 2005899 A2 | 12/2008 |
| EP | 2005900 A2 | 12/2008 |
| EP | 2005901 A1 | 12/2008 |
| EP | 2019633 A1 | 2/2009 |
| EP | 2090247 A1 | 8/2009 |
| EP | 2111803 A2 | 10/2009 |
| EP | 2245993 A2 | 11/2010 |
| EP | 2319424 A1 | 5/2011 |
| EP | 2382928 A1 | 11/2011 |
| FR | 2731895 A1 | 9/1996 |
| GB | 2298905 A | 9/1996 |
| WO | 0154594 A1 | 8/2001 |
| WO | 03094747 A1 | 11/2003 |
| WO | 2007009099 A2 | 1/2007 |
| WO | 2007019268 A2 | 2/2007 |
| WO | 2007102152 A2 | 9/2007 |
| WO | 2008039238 A1 | 4/2008 |
| WO | 2008039249 A1 | 4/2008 |
| WO | 2008039250 A1 | 4/2008 |
| WO | 2008039270 A1 | 4/2008 |
| WO | 2008042021 A1 | 4/2008 |
| WO | 2008042022 A1 | 4/2008 |
| WO | 2008042043 A1 | 4/2008 |

(56) References Cited

FOREIGN PATENT DOCUMENTS

| | | | |
|---|---|---|---|
| WO | 2008042044 A2 | 4/2008 | |
| WO | 2008042045 A2 | 4/2008 | |
| WO | 2008094210 A1 | 8/2008 | |
| WO | 2008141288 A1 | 11/2008 | |
| WO | 2009038550 A1 | 3/2009 | |
| WO | 2010011661 A1 | 1/2010 | |
| WO | 2011044032 A2 | 4/2011 | |
| WO | 2011094700 A1 | 8/2011 | |
| WO | 2012141679 A1 | 10/2012 | |
| WO | 2013151888 A1 | 10/2013 | |
| WO | 2014026170 A2 | 2/2014 | |
| WO | 2014085099 A1 | 6/2014 | |
| WO | 2015063609 A2 | 5/2015 | |
| WO | 2015153324 A1 | 10/2015 | |
| WO | 2015153340 A2 | 10/2015 | |
| WO | 2016033221 A1 | 3/2016 | |

OTHER PUBLICATIONS

Parker, G.; A New Stomach Clamp; 26 Postgrad Med. J. 550; Oct. 1950; 1 page.
Harrah, J. D.; A Lung Clamp for Use with Mechanical Staplers; 28 The Annals of Thoracic Surgery 489; Nov. 1979; 2 pages.
Steichen, F. M. et al.; Stapling in Surgery; Figures 1-11C; Year Book Medical Publishers, Inc.; 1984; 3 pages.
Regan, J. P. et al.; Early Experience with Two-Stage Laparoscopic Roux-en-Y Gastric Bypass as an Alternative in the Super-Super Obese Patient; Obes Surg; 13(6):861-4; Dec. 1, 2003; abstract only; 2 pages.
AtriCure, Inc.; 510(k) Summary for AtriClip LAA Exclusion System with preloaded Gillinov-Cosgrove Clip; published Jun. 10, 2010; 6 pages.
Jacobs, M. et al.; Laparoscopic sleeve gastrectomy: a retrospective review of 1- and 2-year results; Surg Endosc. Apr. 2010; 24(4):781 5; doi: 10.1007/S00464-009-0619-8; Epub Aug. 19, 2009; abstract only; 2 pages.
LAAx, Inc.; 510(k) Summary for TigerPaw(R) System; published Oct. 29, 2010; 6 pages.
Zuckerman, B. D., Food and Drug Administration; Letter to AtriCure, Inc. Addressing Indication for Use of AtriClip LAA Exclusion System w/Pre-loaded Gillnov-Cosgrove Clip; Jun. 10, 2010; 3 pages.
Dept. of Health and Human Services; CMS Description of Open Left Atrial Appendage Occlusion with "U" Fastener Implant; Mar. 9, 2011; 1 page.
Pfiedler Enterprises; Science of Stapling: Urban Legend and Fact; Jun. 4, 2012; 38 pages.

Parikh, M. et al.; Surgical Strategies That May Decrease Leak After Laparoscopic Sleeve Gastrectomy; 257 Annals of Surgery 231; Feb. 2013; 7 pages.
International Search Report and Written Opinion of the International Searching Authority received in International Patent App. No. PCT/US2014/070869; dated Apr. 21, 2015; 17 pages.
International Preliminary Report on Patentability and Written Opinion of the International Searching Authority received in International Patent App. No. PCT/US2015/048740; dated Mar. 7, 2017; 8 pages.
International Search Report and Written Opinion of the International Searching Authority received in International Patent App. No. PCT/US2015/022904; dated Jun. 25, 2015; 6 pages.
International Search Report and Written Opinion of the International Searching Authority received in International Patent App. No. PCT/US2015/022990; dated Sep. 30, 2015; 10 pages.
International Search Report and Written Opinion of the International Searching Authority received in International Patent App. No. PCT/US2015/048740; dated Feb. 17, 2016; 12 pages.
European Search Report received in European Application No. 15774247; dated Dec. 23, 2016; 11 pages.
Supplementary Partial European Search Report received in European Application No. 14872137; dated Dec. 12, 2016; 5 pages.
Supplementary European Search Report received in European Application No. 14872137; dated Mar. 28, 2017; 15 pages.
Supplementary European Search Report received in European Application No. 15772561; dated Mar. 15, 2017; 8 pages.
Examination Report received in European Application No. 15772561; dated Oct. 29, 2018; 7 pages.
International Preliminary Report on Patentability and Written Opinion of the International Searching Authority received in Application No. PCT/US2018/046743; dated Feb. 18, 2020; 17 pages.
International Search Report and Written Opinion of the International Searching Authority received in International Patent App. No. PCT/US2018/046743; dated Dec. 4, 2018; 20 pages.
Search Report received in Chinese Application No. 201480075706. 2; dated Nov. 28, 2018; 3 pages.
Examination Report received in Australian Application No. 2015241193; dated Dec. 11, 2018; 5 pages.
Examination Report received in Australian Application No. 2015241267; dated Feb. 25, 2019; 6 pages.
Examination Report received in Australian Application No. 2016208416; dated May 18, 2017; 4 pages.
Examination Report received in Australian Application No. 2018203527; dated Oct. 22, 2018; 5 pages.
International Search Report and Written Opinion of the International Searching Authority received in International Patent Appln. No. PCT/US2022/021250; dated Jun. 10, 2022; 12 pages.

* cited by examiner

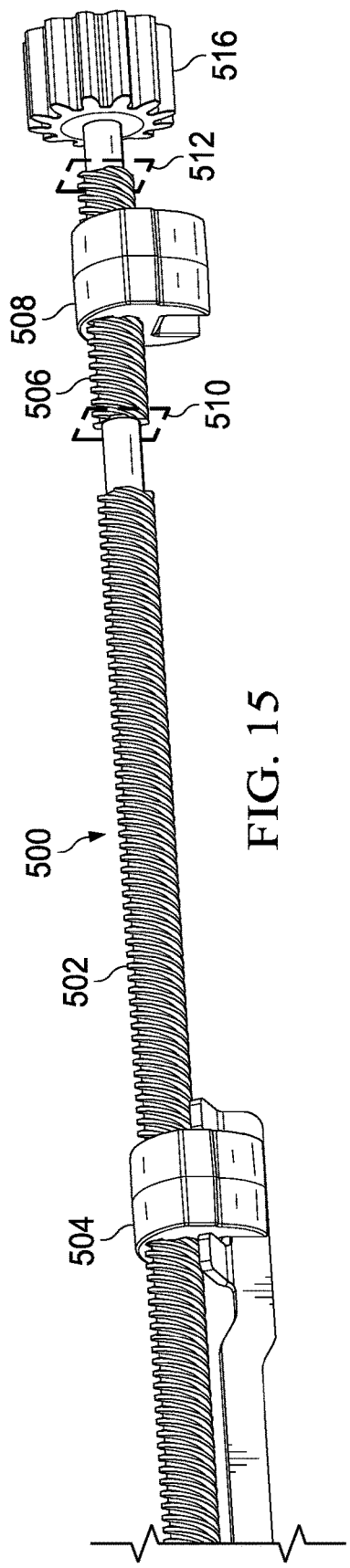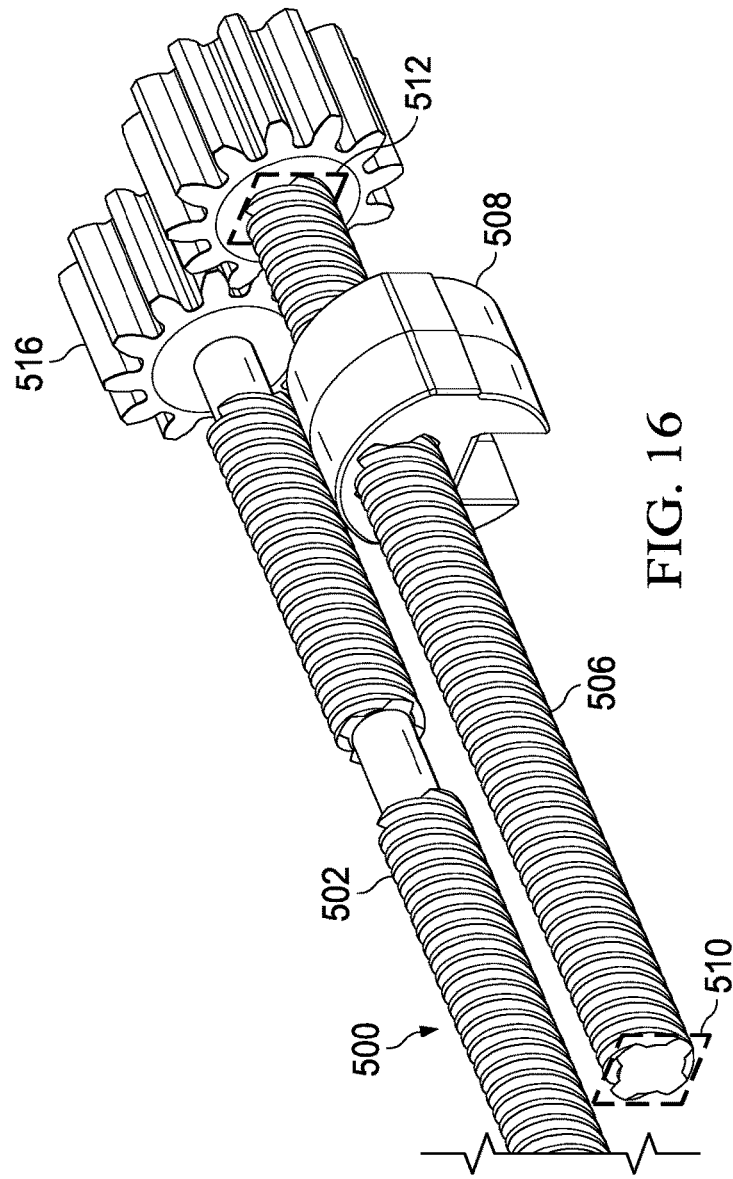
FIG. 15
FIG. 16

SYSTEMS AND METHODS FOR PREVENTING TISSUE MIGRATION IN SURGICAL STAPLERS

CROSS REFERENCE TO RELATED APPLICATIONS

This application claims the priority benefit of U.S. Provisional Patent Application No. 63/164,837, filed Mar. 23, 2021, which is hereby incorporated herein by reference in its entirety.

BACKGROUND

The disclosed inventive subject matter relates in general to medical devices and surgical instruments and more specifically to systems, devices, and methods associated with surgical staplers used for bariatric surgery performed using laparoscopic techniques.

Vertical sleeve gastrectomy is a commonly performed type of bariatric surgery in which a surgical stapling instrument is used to remove a portion of the stomach and staple the remaining portion of the stomach closed. Stapling instruments used for this procedure typically include an upper jaw that is connected to a lower jaw at one end thereof using a hinge. Such devices usually include a tissue stop at or near the hinge to prevent the undesirable migration of tissue into the hinged region of the stapler during use. More recently developed stapling instruments such as the TITAN® SGS23R (Standard Bariatrics) and similar instruments include an upper jaw that is connected to a lower jaw at two locations, namely at both ends of the jaws. Staplers having this design include a distal tissue stop and a proximal tissue stop formed on the lower jaws thereof. However, when in the stapler is in an open position, an area exists between the jaws adjacent to the proximal tissue stop into which tissue may migrate during use of the instrument. This migration may continue until a certain degree of closure is reached, at which point the upper jaw engages the proximal tissue stop of the lower jaw to create a tissue barrier. If a surgeon inadvertently closes the stapler on stomach tissue outside the portion of the instrument that ejects staples, transection of tissue without mechanical fastening thereof with staples may result. If this situation is not recognized by the surgeon during the medical procedure, post-operative complications such as leaks may occur. Because this is an undesirable outcome, an additional barrier or other means of preventing tissue migration in surgical stapling instruments would be beneficial.

SUMMARY

The following provides a summary of certain example implementations of the disclosed inventive subject matter. This summary is not an extensive overview and is not intended to identify key or critical aspects or elements of the disclosed inventive subject matter or to delineate its scope. However, it is to be understood that the use of indefinite articles in the language used to describe and claim the disclosed inventive subject matter is not intended in any way to limit the described inventive subject matter. Rather the use of "a" or "an" should be interpreted to mean "at least one" or "one or more".

One implementation of the disclosed technology provides a system for preventing unwanted tissue migration in surgical staplers, comprising a surgical stapler having an end effector for dispensing surgical staples, wherein the end effector includes an upper jaw the upper jaw including a proximal end and a distal end; a lower jaw, the lower jaw including a proximal end and a distal end, wherein the distal end of the upper jaw is connected to the distal end of the lower jaw, and wherein the proximal end of the upper jaw is connected to the proximal end of the lower jaw; a first tissue stop formed on the distal end of the lower jaw; a second tissue stop formed on the proximal end of the of the lower jaw, wherein the second tissue stop and the proximal end of the upper jaw define a no tissue zone when the surgical stapler is in an open position; and a tissue cutting device disposed within the lower jaw for resecting tissue; and a warning, blocking, impeding, or barrier forming device for preventing the unwanted migration of tissue into the no tissue zone during surgical procedures such that resection of unstapled tissue is prevented.

The warning, blocking, impeding, or barrier forming device may include at least one warning label placed on the stapler for alerting a user of the stapler to the no tissue zone. The warning, blocking, impeding, or barrier forming device may include a flexible sheath, wherein the flexible cape is placed partially or completely around the proximal ends of the upper and lower jaws while permitting the opening and closing thereof. The warning, blocking, impeding, or barrier forming device may include a rigid shield, wherein the rigid shield is formed on or attached to the proximal end of the upper jaw. The warning, blocking, impeding, or barrier forming device may include a flexible band attached to the upper jaw and to the lower jaw and extending therebetween, and wherein at least a portion of the flexible band is located in front of the second tissue stop. The warning, blocking, impeding, or barrier forming device may include a post extending between the upper jaw and the lower jaw at the front end of the second tissue stop, wherein the post either rotates or telescopes when the jaws open and close. The warning, blocking, impeding, or barrier forming device may include a curved or hinged closure link extending between the proximal ends of the upper jaw and the lower jaw. The warning, blocking, impeding, or barrier forming device may include a sacrificial band of compliant material, block of compliant material, or compliant balloon positioned between the proximal ends of the upper jaw and the lower jaw. The warning, blocking, impeding, or barrier forming device may include a non-sacrificial block of rigid material or piece of expandable material positioned between the proximal ends of the upper jaw and the lower jaw and adapted to permit the tissue cutting device to pass therethrough.

Another implementation of the disclosed technology provides a system for preventing unwanted tissue migration in surgical staplers, comprising a surgical stapler having an end effector for dispensing surgical staples, wherein the end effector includes an upper jaw the upper jaw including a proximal end and a distal end; a lower jaw, the lower jaw including a proximal end and a distal end, wherein the distal end of the upper jaw is connected to the distal end of the lower jaw, and wherein the proximal end of the upper jaw is connected to the proximal end of the lower jaw; a first tissue stop formed on the distal end of the lower jaw; a second tissue stop formed on the proximal end of the of the lower jaw, wherein the second tissue stop and the proximal end of the upper jaw define a no tissue zone when the surgical stapler is in an open position; and a tissue cutting device disposed within the lower jaw for resecting tissue; and a mechanism for preventing the unwanted migration of tissue into the no tissue zone during surgical procedures such that resection of unstapled tissue is prevented.

The mechanism may disengage the tissue cutting device before it reaches the no tissue zone. The mechanism may stop the tissue cutting device before it reaches the no tissue zone and reverses its direction of travel toward the distal end of the lower jaw. The mechanism may use software or software and sensors associated with the operation of the stapler for detecting the presence of tissue within the no tissue zone and taking corrective action. The system may also include audible, visual, or tactile indicators, or various combinations thereof, that are triggered by the software or software and sensors when the presence of tissue is detected within the no tissue zone.

Another implementation of the disclosed technology provides a method for preventing unwanted tissue migration in a surgical stapler having an end effector for dispensing surgical staples, wherein the end effector includes an upper jaw having proximal end and a distal end; a lower jaw having a proximal end and a distal end, wherein the distal end of the upper jaw is connected to the distal end of the lower jaw, and wherein the proximal end of the upper jaw is connected to the proximal end of the lower jaw; a first tissue stop formed on the distal end of the lower jaw; a second tissue stop formed on the proximal end of the of the lower jaw, wherein the second tissue stop and the proximal end of the upper jaw define a no tissue zone when the surgical stapler is in an open position; and a tissue cutting device disposed within the lower jaw for resecting tissue, the method comprising providing a warning, blocking, impeding, or barrier forming device for preventing the unwanted migration of tissue into the no tissue zone during surgical procedures such that resection of unstapled tissue is prevented; or providing a mechanism for preventing the unwanted migration of tissue into the no tissue zone during surgical procedures such that resection of unstapled tissue is prevented.

The warning, blocking, impeding, or barrier forming device may include at least one warning label placed on the stapler for alerting a user of the stapler to the no tissue zone. The warning, blocking, impeding, or barrier forming device may include a flexible sheath, wherein the flexible cape is placed partially or completely around the proximal ends of the upper and lower jaws while permitting the opening and closing thereof. The warning, blocking, impeding, or barrier forming device may include a rigid shield, wherein the rigid shield is formed on or attached to the proximal end of the upper jaw. The warning, blocking, impeding, or barrier forming device may include a flexible band attached to the upper jaw and to the lower jaw and extending therebetween, and wherein at least a portion of the flexible band is located in front of the second tissue stop. The warning, blocking, impeding, or barrier forming device may include a post extending between the upper jaw and the lower jaw at the front end of the second tissue stop, wherein the post either rotates or telescopes when the jaws open and close. The warning, blocking, impeding, or barrier forming device may include a curved or hinged closure link extending between the proximal ends of the upper jaw and the lower jaw. The warning, blocking, impeding, or barrier forming device may include a sacrificial band of compliant material, block of compliant material, or compliant balloon positioned between the proximal ends of the upper jaw and the lower jaw. The warning, blocking, impeding, or barrier forming device may include a non-sacrificial block of rigid material or piece of expandable material positioned between the proximal ends of the upper jaw and the lower jaw and adapted to permit the tissue cutting device to pass therethrough. The mechanism may disengage the tissue cutting device before it reaches the no tissue zone. The mechanism may stop the tissue cutting device before it reaches the no tissue zone and reverses its direction of travel toward the distal end of the lower jaw. The mechanism may use software or software and sensors associated with the operation of the stapler for detecting the presence of tissue within the no tissue zone and taking corrective action Audible, visual, or tactile indicators, or various combinations thereof, that are triggered by the software or software and sensors when the presence of tissue is detected within the no tissue zone, may also be provided.

It should be appreciated that all combinations of the foregoing concepts and additional concepts discussed in greater detail below (provided such concepts are not mutually inconsistent) are contemplated as being part of the inventive subject matter disclosed herein and may be implemented to achieve the benefits as described herein. Additional features and aspects of the disclosed system, devices, and methods will become apparent to those of ordinary skill in the art upon reading and understanding the following detailed description of the example implementations. As will be appreciated by the skilled artisan, further implementations are possible without departing from the scope and spirit of what is disclosed herein. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more example implementations of the disclosed inventive subject matter and, together with the general description given above and detailed description given below, serve to explain the principles of the disclosed subject matter, and wherein:

FIG. 15 depicts an implementation that utilizes a reversing knife approach to preventing the transection of tissue without closure thereof with surgical staples through the inclusion of a secondary thread on the primary firing screw;

FIG. 16 depicts an implementation that utilizes a reversing knife approach to preventing the transection of tissue without the closure thereof with surgical staples through the inclusion of a secondary fine thread on an auxiliary firing screw;

DETAILED DESCRIPTION

Figure 1A:
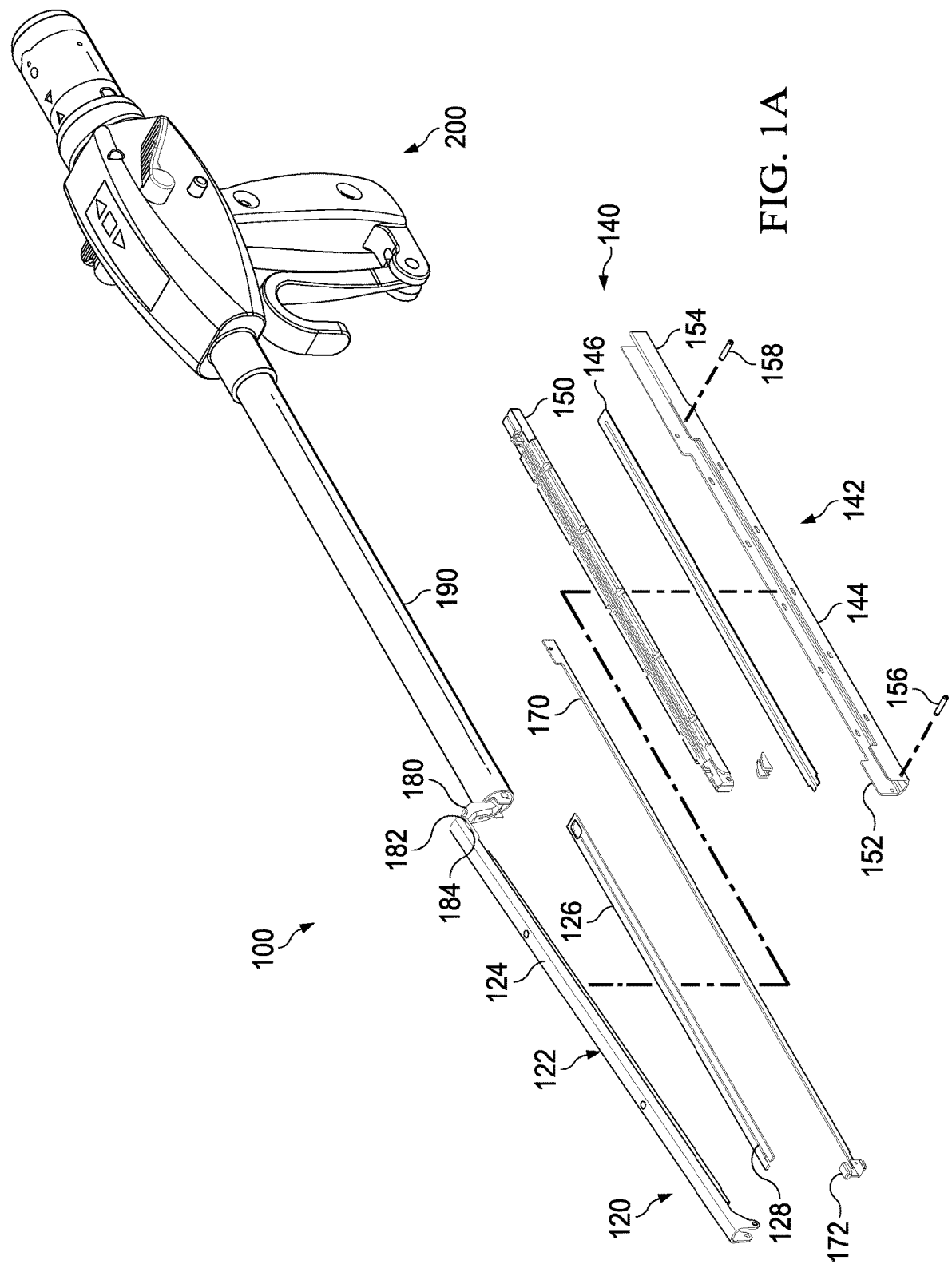
FIGS. 1A and 1B depict, in an exploded view and a perspective view, respectively, an example surgical stapler that is hinged at two locations along the length of the stapler and that includes a no tissue zone into which tissue may unwantedly migrate during surgical procedures such as laparoscopic bariatric surgery.

Example implementations are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the disclosed inventive subject matter. Accordingly, the following implementations are set forth without any loss of generality to, and without imposing limitations upon, the claimed subject matter.

As previously stated, surgical stapling instruments such as the TITAN® SGS23R (Standard Bariatrics) include an upper jaw that is connected to a lower jaw at two locations, namely at both ends of the jaws. Staplers having this design can include a distal tissue stop and a proximal tissue stop formed on the lower jaws thereof. However, when the stapler is in an open position, an area may exist between the jaws adjacent to the proximal tissue stop into which tissue may migrate during use of the instrument. This migration may be problematic if a surgeon inadvertently closes the stapler on stomach tissue that has migrated outside the portion of the instrument that ejects and secures tissue with staples. In such an area, where tissue has not been stapled, transection of tissue may still progress resulting in a potentially dangerous unstapled portion of the transected tissue. If this situation is not recognized by the surgeon during the medical procedure, post-operative complications such as leaks may occur. Disclosed implementations provide various structural and mechanical systems, devices, and methods for preventing the unwanted migration of tissue when staplers such as the TITAN® SGS23R are used in laparoscopic bariatric surgery.

Staplers compatible with the disclosed technology are described in U.S. Pat. No. 10,687,814, which is incorporated by reference herein in its entirety, for all purposes. Some implementations of the staplers disclosed in U.S. Pat. No. 10,687,814 include end effectors that are attached to a support tube that is attached to a handle that includes an actuator for the instrument. As shown in the Figures of U.S. Pat. No. 10,687,814, example end effectors found on surgical staplers include an upper jaw connected to a lower jaw by a simple hinge at the distal end of the stapler and by a master link or rigid link at the proximal end of the stapler. The upper jaw may include an anvil assembly that further includes an anvil frame, an anvil plate, and an anvil plate channel formed therein. The lower jaw may include a cartridge assembly that further includes a cartridge frame, a cartridge plate with a cartridge plate channel formed therein, and a cartridge for containing surgical staples. The cartridge frame may include a first tissue stop and a second tissue stop as well as first and second cartridge pins. A blade assembly that includes a cutting blade is disposed within the cartridge assembly. The master link may include a master link pin that cooperates with a master link slot.

Figure 1B:
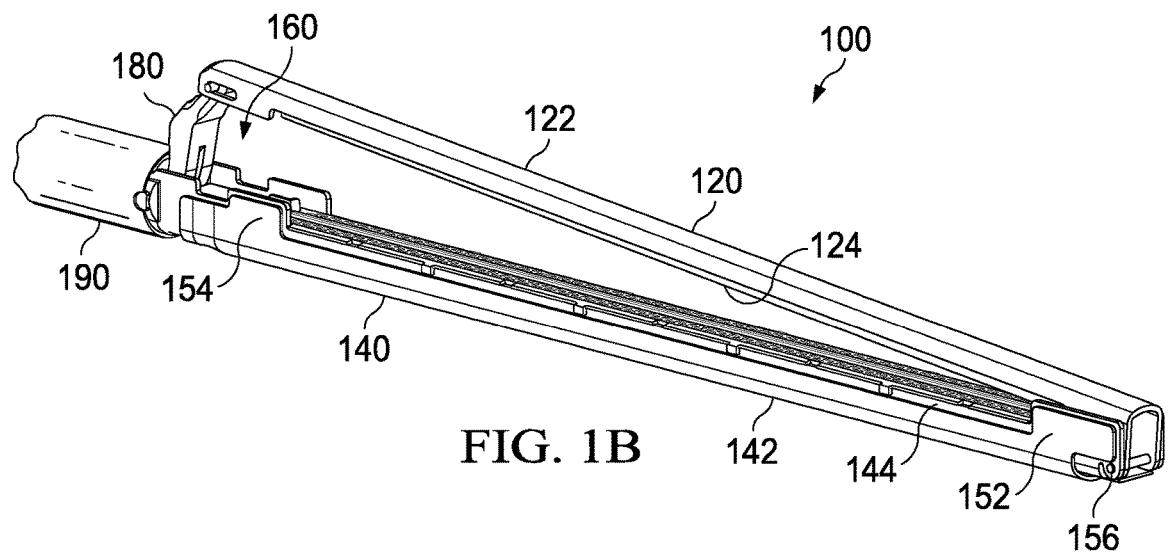

FIGS. 1A-1B depict example surgical stapler having end effector 100 (e.g., TITAN® SGS23R), which includes upper jaw 120, lower jaw 140, blade/knife assembly 170, and master link 180. Upper jaw 120 includes anvil assembly 122, which further includes anvil frame 124, anvil plate 126, and anvil plate channel 128. Lower jaw 140 includes cartridge assembly 142, which further includes cartridge frame 144, cartridge plate 146, cartridge 150, distal tissue stop 152, proximal tissue stop 154, distal cartridge pin 156, and proximal cartridge pin 158. Distal cartridge pin 156 connects upper jaw 120 and lower jaw 140 in a hinged manner at the distal end of end effector 100. Blade/knife assembly 170, which includes I-beam or I-shaped knife 172 (see also FIG. 9) is disposed within lower jaw 140. Master link 180 connects upper jaw 120 and lower jaw 140 at the proximal end of end effector 100 in a hinged manner using master pin 182, which is positioned in a sliding manner within master link slot 184. End effector 100 is attached to elongated support tube 190, which is connected to handle 200 (see also FIGS. 5 and 6). Handle 200 includes various mechanical aspects that actuate end effector 100 and knife 172. A region of concern or "no tissue zone" 160 can be any area or space into which tissue may unwantedly migrate during surgical procedures such as laparoscopic bariatric surgery. No tissue zone 160 may be located at the proximal end of the end effector, for example, but may be any area where tissue migration is problematic.

Figure 2:
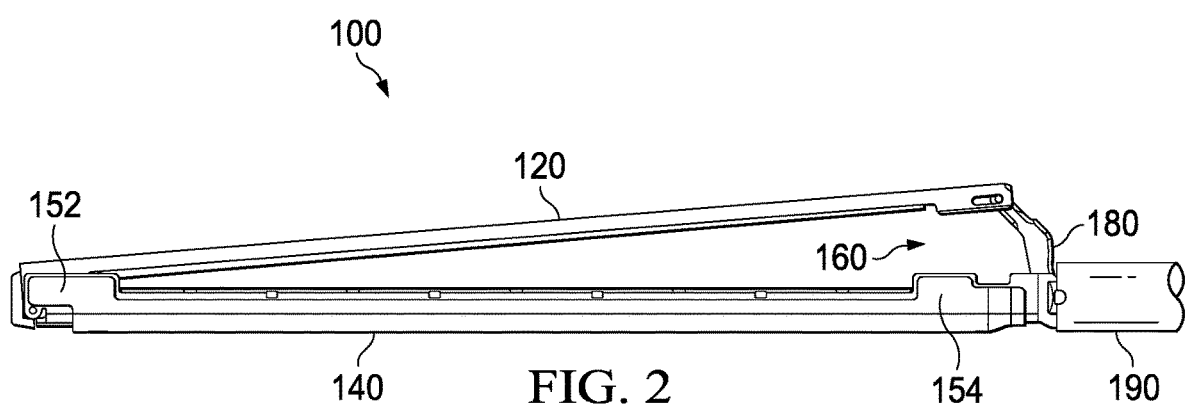
FIG. 2 depicts the surgical stapler of FIG. 1A, wherein a physical label has been placed on the lower jaw of the stapler indicating that "no tissue" is to be situated within the labeled region.

FIG. 2 depicts an example labeling solution to the tissue migration concern. FIG. 2 depicts the surgical stapler of FIG. 1B, wherein a physical label has been placed on the lower jaw of end effector 100 indicating that "no tissue" is to be situated within the labeled region, which is no tissue zone 160). "No tissue" graphics may also be included on top of anvil assembly 122, on upper jaw 120, on the side of cartridge assembly 142, on lower jaw 140, or on any other surface of end effector 100 to alert the user of the risk. Labeling may be affixed to end effector 100 using adhesive, or by screen printing, laser etching, or the like, and may include additional or alternate phrases, as wells as various fonts, colors, and graphics intended to draw the attention of a user to the no tissue zone.

Figure 3:
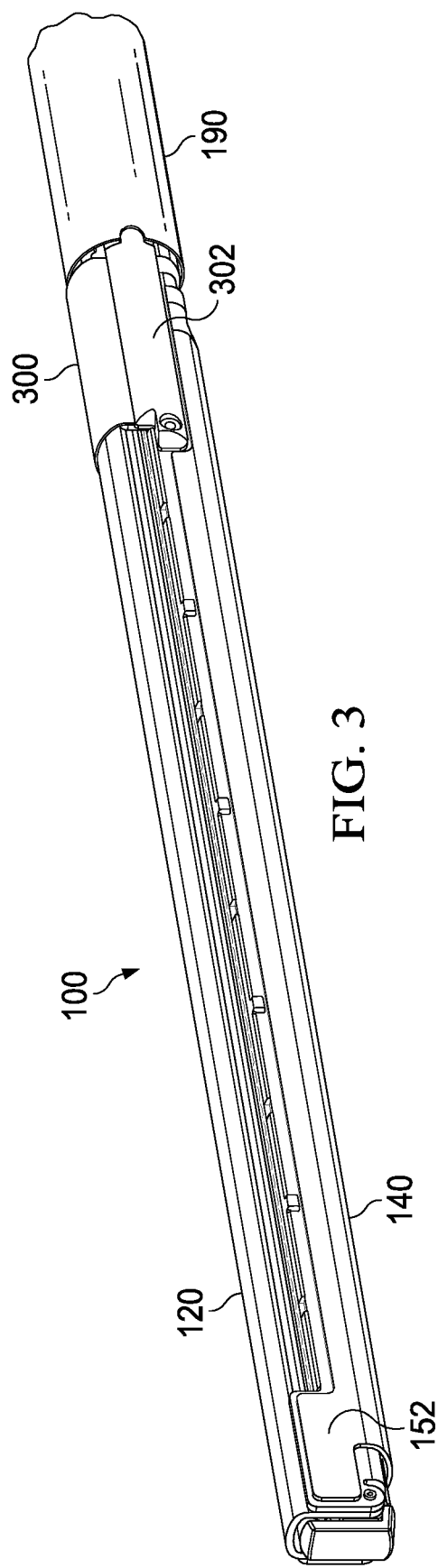
FIG. 3 depicts the stapler of FIG. 1A, wherein the jaws of the stapler are shown in a closed position and wherein a flexible tissue-blocking sheath has been partially wrapped around the upper and lower jaws of the stapler.
Figure 4:
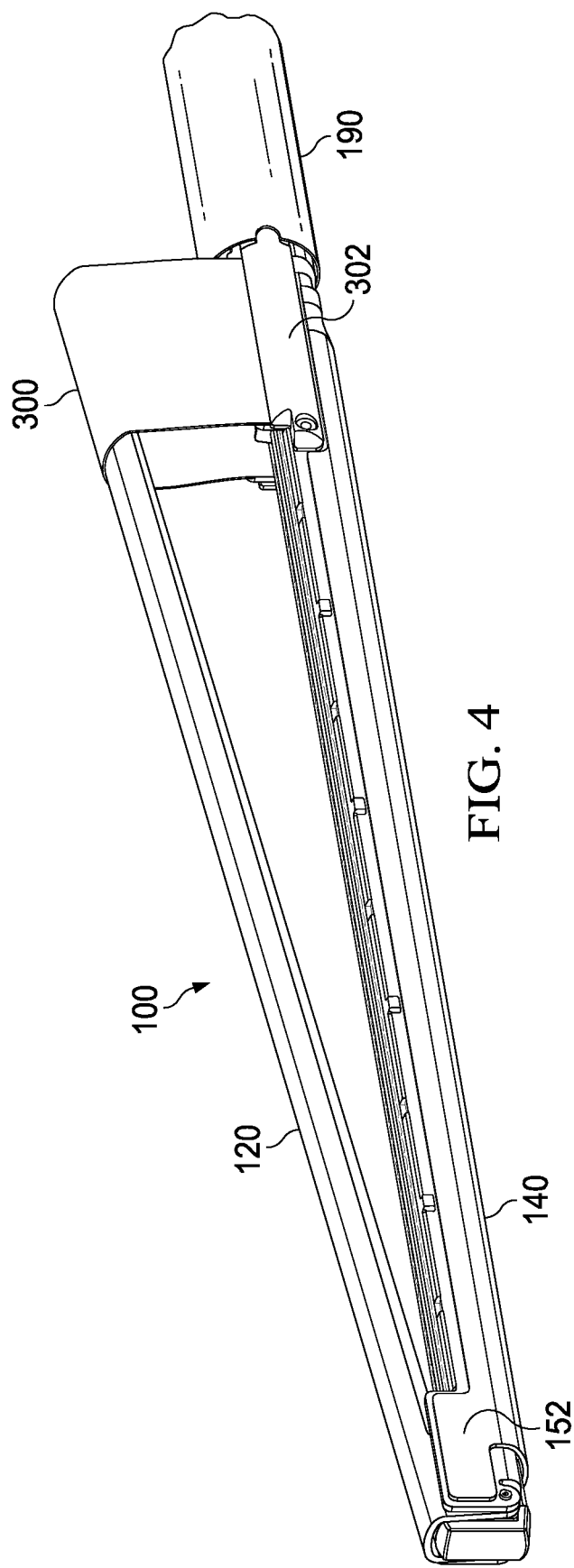
FIG. 4 depicts the stapler of FIG. 1A, wherein the jaws of the stapler are shown in an open position and wherein a flexible tissue-blocking sheath has been partially wrapped around the upper and lower jaws of the stapler.
Figure 5:
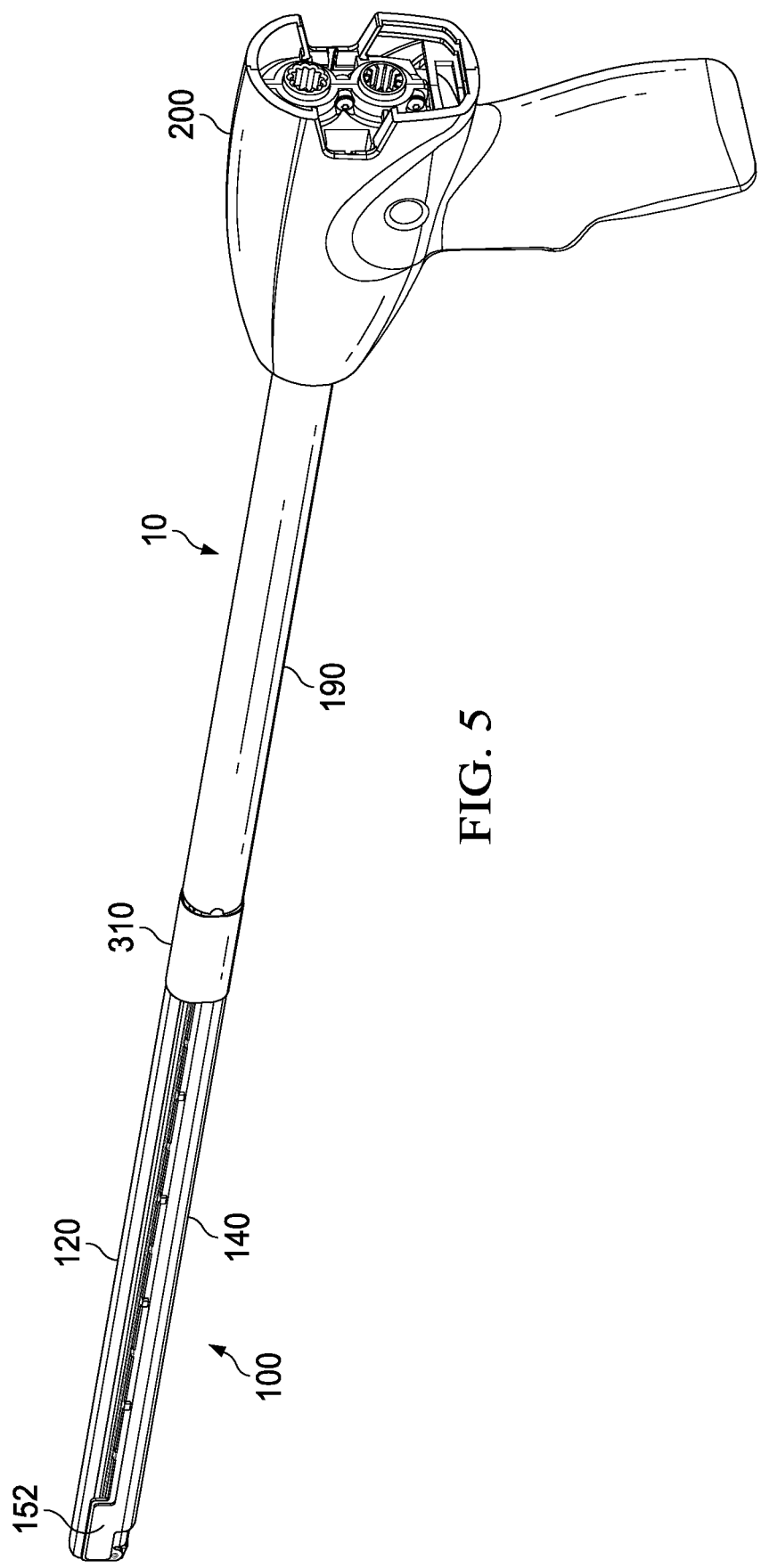
FIG. 5 depicts the stapler of FIG. 1A, wherein the jaws of the stapler are shown in a closed position and wherein a flexible tissue-blocking sleeve has been circumferentially wrapped around the upper and lower jaws of the stapler.
Figure 6:
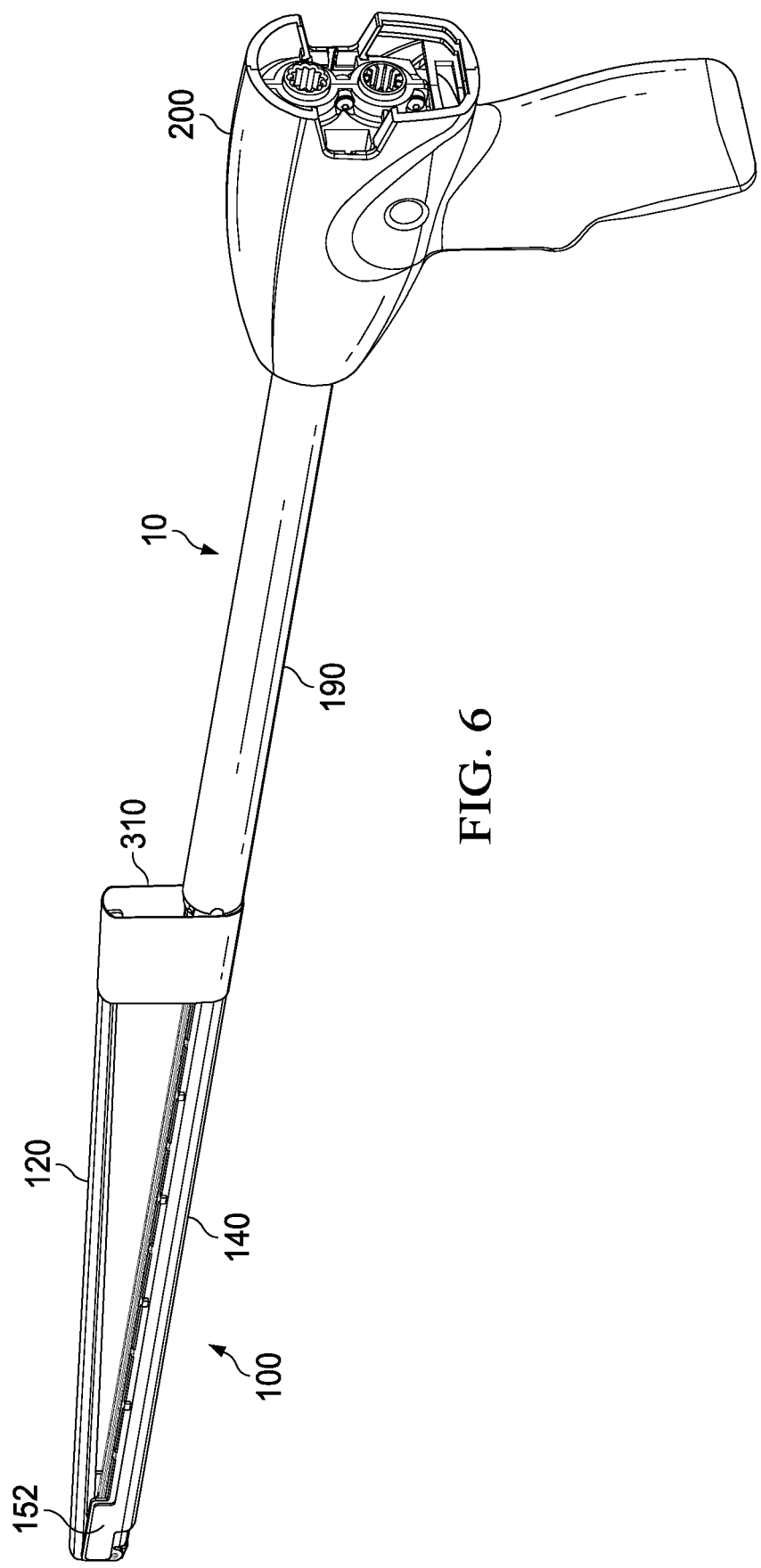
FIG. 6 depicts the stapler of FIG. 1A, wherein the jaws of the stapler are shown in an open position and wherein a flexible tissue-blocking sleeve has been circumferentially wrapped around the upper and lower jaws of the stapler.
Figure 7:
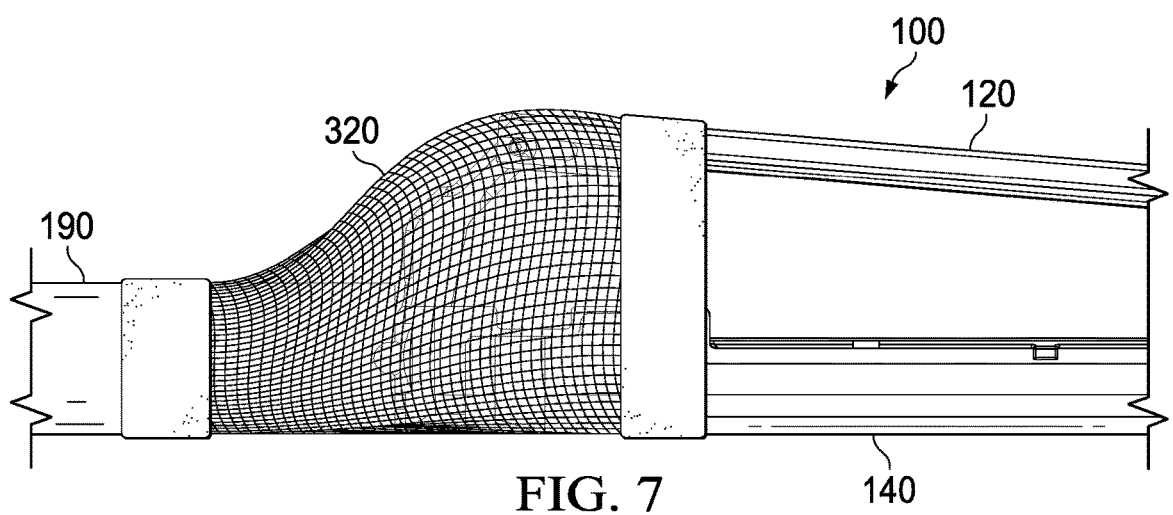
FIG. 7 depicts the stapler of FIG. 1A, wherein the jaws of the stapler are shown in an open position and wherein a flexible, braided, tissue-blocking sleeve has been circumferentially wrapped around the upper and lower jaws of the stapler
Figure 8:
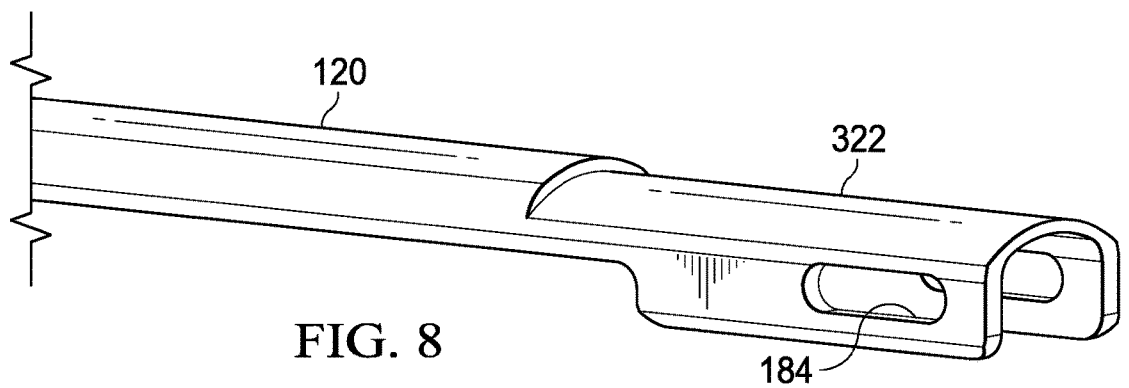
FIG. 8 depicts the upper jaw of the stapler of FIG. 1A, wherein a recessed region has been formed therein for accommodating a flexible sheath or sleeve.

FIGS. 3-8 depict various implementations of a tissue-blocking shield placed around the jaws of end effector 100 for the purpose preventing tissue from migrating into region 160 while still permitting the jaws of end effector 100 to open. FIG. 3 depicts the stapler of FIG. 1B, wherein the jaws of end effector 100 are shown in a closed position and flexible tissue-blocking sheath 300 has been partially wrapped around upper and lower jaws 120 and 140 of end effector 100. FIG. 4 depicts the stapler of FIG. 1B, where the jaws of end effector 100 are shown in an open position and flexible tissue-blocking elastomeric sheath 300 has been partially wrapped around upper and lower jaws 120 and 140 of end effector 100. Sheath lock 302 is included in this implementation for locking cape 300 on end effector 100. Sheath lock 302 may be an overmolded plastic component located on either side of lower jaw 140. Sheath lock 302 may be affixed to lower jaw 140 with a screw or other positive fixation device such as a rivet, pin, orbital rivet, or heat stake. The proximal end of sheath lock 302 is affixed to lower jaw 140 by engaging an interlocking feature in support tube 190. Sheath lock 302 may incorporate a jaw lock component or may engage with a jaw lock to constrain the sheath lock FIG. 5 depicts the end effector of FIG. 1B, where the jaws of end effector 100 are shown in a closed position and elastomeric tissue-blocking sleeve 310 has been circumferentially wrapped around upper and lower jaws 120 and 140 of end effector 100. FIG. 6 depicts the end effector of FIG. 1B, where the jaws of end effector 100 are shown in an open position and elastomeric tissue-blocking sleeve 310 has been circumferentially wrapped around upper and lower jaws 120 and 140 of end effector 100. FIG. 7 depicts the end effector of FIG. 1B, wherein the jaws of end effector 100 are shown in an open position and flexible, braided mesh barrier 320 has been circumferentially wrapped around upper and lower jaws 120 and 140 of end effector 100. FIG. 8 depicts upper jaw 120 of the end effector of FIG. 1B, wherein recessed region 322 has been formed therein for accommodating a flexible cape or sleeve.

The sheath and sleeve described above may be made from a variety of elastic materials including silicone, urethane, or the like, or may be geometrically flexible such as the braided implementation of FIG. 7. The implementation shown in FIG. 7 may include bands placed on both ends of the sleeve to prevent the sleeve from fraying. Alternately, both ends of the sleeve may be overmolded with an elastomeric material to prevent the sleeve from fraying. The sheath and sleeve may be lubricated to minimize drag force when inserting the stapling instrument into a trocar. Lubrication may be achieved by altering the surface finish of the sheath, adding a lubricant to the sheath such as a silicone grease, polytetrafluoroethylene (PTFE) solids or the like, or by doping the sheath material with a lubricant. Adding a stainless steel or plastic spine (not shown) to the top of the sheath may also reduce drag force. The spine may be over-molded to the sheath or rigidly attached to anvil frame 124 by the use of screws or snaps, or by welding, gluing, or other process. Sheath lock 302 member fixes sheath 300 to end effector 100 and may be made of a metal such as stainless steel, or a plastic such as nylon, and may be attached to cartridge frame 144 by a screws, snaps, or other devices. Sheath 300 and sheath lock 302 may be separate components or a single component installed on end effector 100 by over-molding sheath 300 to sheath lock 302. Sheath lock 302 may incorporate a jaw lock component or may engage with a jaw lock to constrain the sheath lock. The previously described no tissue zone labeling may be included on some or all variants of sheath 300.

Figure 9:
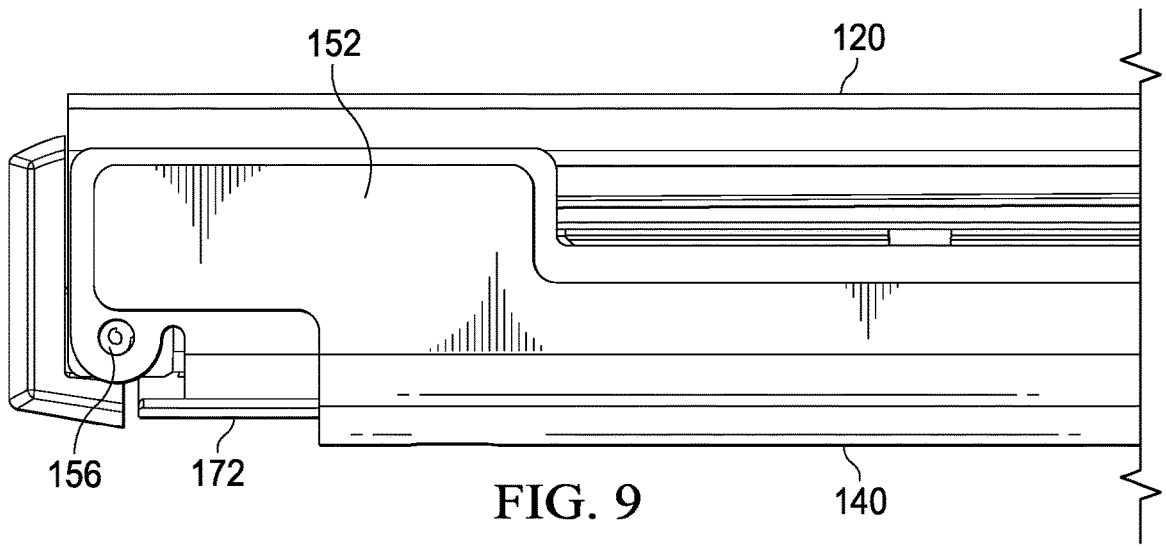
FIG. 9 depicts the stapler of FIG. 1A in a closed position, wherein the tissue cutting knife, also referred to as an I-beam or I-shaped blade, is visible near the distal pin.

FIG. 9 depicts end effector 100 in a closed position where tissue cutting knife 172, also referred to as an I-beam or I-shaped blade, is visible near distal pin 156. Regarding FIG. 9, one implementation of the disclosed technology provides a reversing knife solution to the previously discussed tissue migration concern. This approach eliminates the problem of transecting unstapled tissue by stopping knife 172 before it reaches the no tissue zone at the proximal end of the end effector 100. After transecting only stapled portions of tissue, the knife 172 can be distally to its starting position, tangent to distal pin 156, as shown in FIG. 9. Using this method, knife 172 will not cut tissue without also firing staples along the cut line.

The solution reversing the knife 172, as described above, may be accomplished using software included with commercially available stapling instruments such as, for example, the TITAN® SGS23R "Standard Power Unit" (SPU) software. Once a knife band (see U.S. Pat. No. 10,687,814) activates a limit switch at the proximal limit of firing, such as at the proximal end of the end effector 100, the SPU software can reverse the polarity of the firing motor, to reverse the direction of the knife band. To stop the I-Beam from striking the distal pin 156 when reversing the knife, the SPU can actively monitor the presence of the I-Beam at the distal tip of the end effector 100. A distal limit switch may be attached to end effector 100, stopping the firing motor when the I-Beam has reached its distal position (see FIG. 9). The distal limit switch may be a digital switch that operates in a binary on/off nature depending on whether the I-Beam is at its distal position or not, or an analog sensor that provides a range of values depending on where the I-Beam is located in the firing stroke. If the switch is binary, it may be an off-the-shelf (OTS) single pole single throw (SPST) limit switch that is mounted to a printed circuit board (PCB), a stand-alone OTS limit switch wired back to the SPU by way of a power cable, or a custom limit switch consisting of a movable component that electrically connects (normally open, "NO") or disconnects (normally closed, "NC"), two terminals connected to the SPU. In one implementation, the I-Beam and distal pin 156 cooperate to complete an electric connection and act as a binary switch. If the switch is analog, it may be an OTS analog sensor that is mounted to a PCB or a stand-alone OTS limit switch wired back to the SPU by way of a power cable such as a proximity sensor, ultrasonic sensor, time of light sensor (ToF), laser sensor, light detecting and ranging (LIDAR) sensor, or the like, or a custom analog sensor connected to the SPU. Some implementations include various indicators such as, for example, audible, visual, or tactile indicators, or combinations thereof, that are triggered by the software and sensors when the presence of tissue is detected within no tissue zone 160.

In some implementations, a rotary encoder is included with the firing motor to stop the I-Beam from crashing into distal pin 156 when reversing knife 172, to provide closed-loop feedback of the motor's rotary position. With an encoder, the SPU software monitors the number of motor turns required to activate the proximal firing limit switch and repeats the same number of motor turns to return the knife band to its starting position. Suitable motor encoder technology may be mechanical, optical, or magnetic (hall-effect) to track the rotation of the motor shaft. The SPU may also monitor real-time electrical motor current in amperes to compare to preset current limits when using a device such as the TITAN® SGS23R. The current limits may mitigate damage to the device when in use. The SPU may further monitor the firing motor current when reversing the knife, monitoring for a current spike above a preset threshold to determine when the I-Beam contacts distal pin 156. System software may, for example, only monitor for the current spike at a percentage of the return sequence by means of time or using an encoder as described above. In a similar manner, in an alternate implementation, the SPU monitors the closure motor current for the presence of tissue in the no tissue zone. Tissue in the no tissue zone induces a spike in current on the closure motor within a fixed window of time or closure stroke. Identifying this minimum current spike allows the SPU to detect tissue in the no tissue zone and warn the user of imminent tissue damage and/or prevent the user from firing the device.

Figure 10:
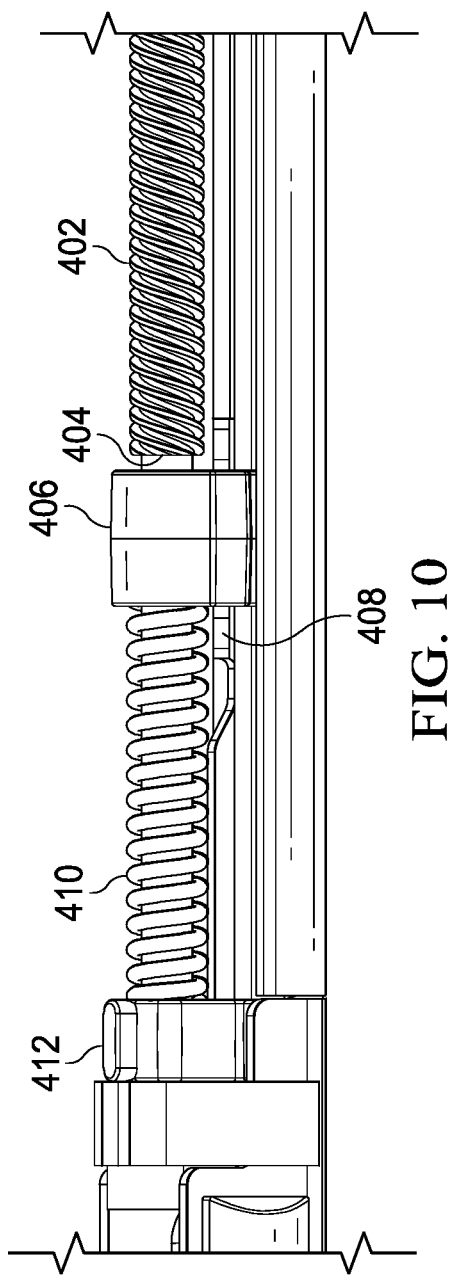
FIG. 10 depicts a mechanical method for stopping the I-Beam from crashing into the distal pin when reversing the knife, wherein the threads on the firing lead screw stop distally, passively limiting the reverse travel of the firing nut.

FIG. 10 depicts another implementation for stopping the I-Beam from striking distal pin 156 when reversing knife 172, wherein the threads on firing lead screw 402 stop distally, passively limiting the reverse travel of firing nut 406. In this implementation, firing nut 406 exhausts the threads on firing lead screw 402 and slips on the threads as firing lead screw 402 continues to turn to drive firing nut 406 distally. Fixed firing screw compression spring 410 applies a load proximally on firing nut 406 and allows firing nut 406 to reengage with firing lead screw 402 when firing lead screw 402 rotates to drive firing nut 406 proximally. Fixed firing lead screw 402 is constrained laterally by firing bushing 412 and the threads of firing lead screw 402, limited by its inner diameter (ID) being less than the major diameter of the threads of firing lead screw 402.

Figure 11:
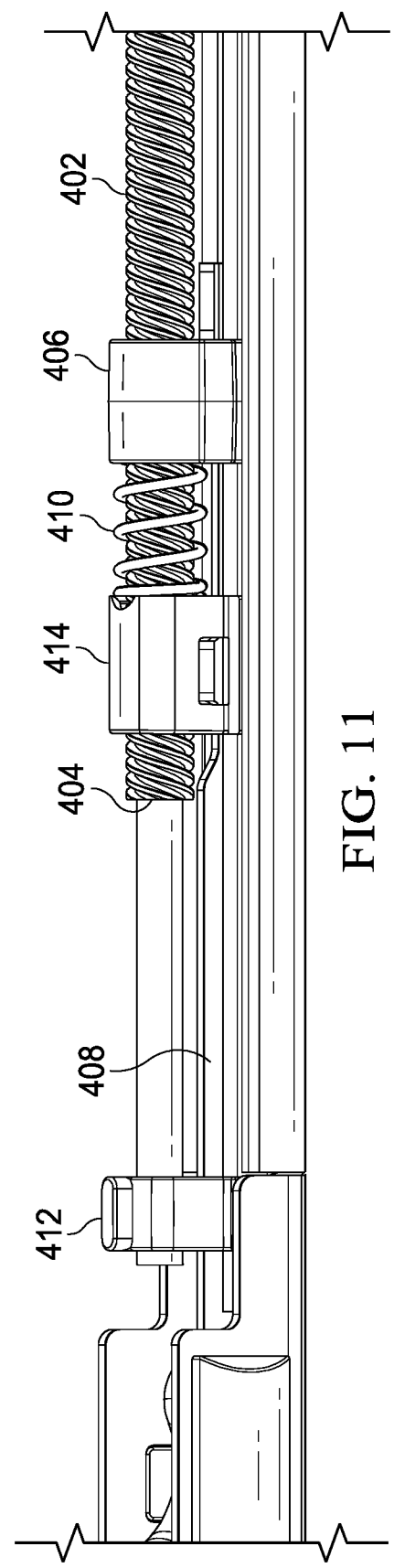
FIG. 11 depicts a mechanical method for stopping the I-Beam from striking the distal pin when reversing the knife, where the threads on the firing lead screw stop distally, passively limiting the reverse travel of the firing nut, but where the firing screw compression spring is mobile rather than fixed.

FIG. 11 depicts another implementation for stopping the I-Beam from crashing into distal pin 156 when reversing knife 172, wherein the threads on firing screw 402 stop distally, passively limiting the reverse travel of firing nut 406, but where firing screw compression spring 410 is mobile rather than fixed. In this implementation, mobile firing screw compression spring 410 is constrained by nut plate 414 and firing nut 406, and spring 410 travels along the threaded and unthreaded portion of firing lead screw 402 as firing nut 406 and nut plate 414 travel. Nut plate 414 is unthreaded, unlike firing nut 406, and slides along the threaded and unthreaded portion of firing lead screw 402 like mobile firing screw compression spring 410. When firing nut 406 exhausts the threads on firing lead screw 402, it will slip on the threads as firing lead screw 402 continues to turn to drive firing nut 406 distally. Unlike the previous implementation, this variant anticipates a crash of the I-Beam and distal pin 156, but mobile firing screw compression spring 410 provides a compliant power transfer from firing nut 406 and knife band 408 when firing nut 406 is driven distally.

Figure 12:
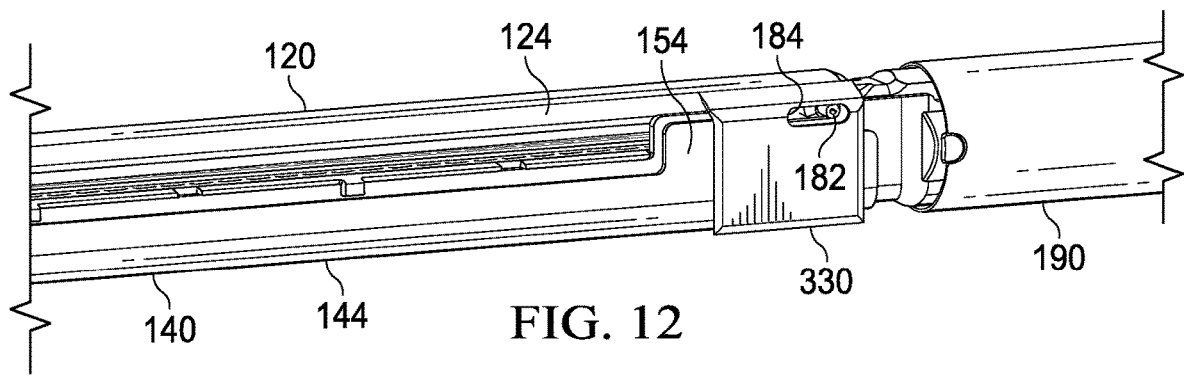
FIG. 12 depicts the stapler of FIG. 1A, where the jaws of the stapler are shown in a closed position and where a tissue-blocking anvil cap has been formed or placed on the upper jaw of the stapler.
Figure 13:
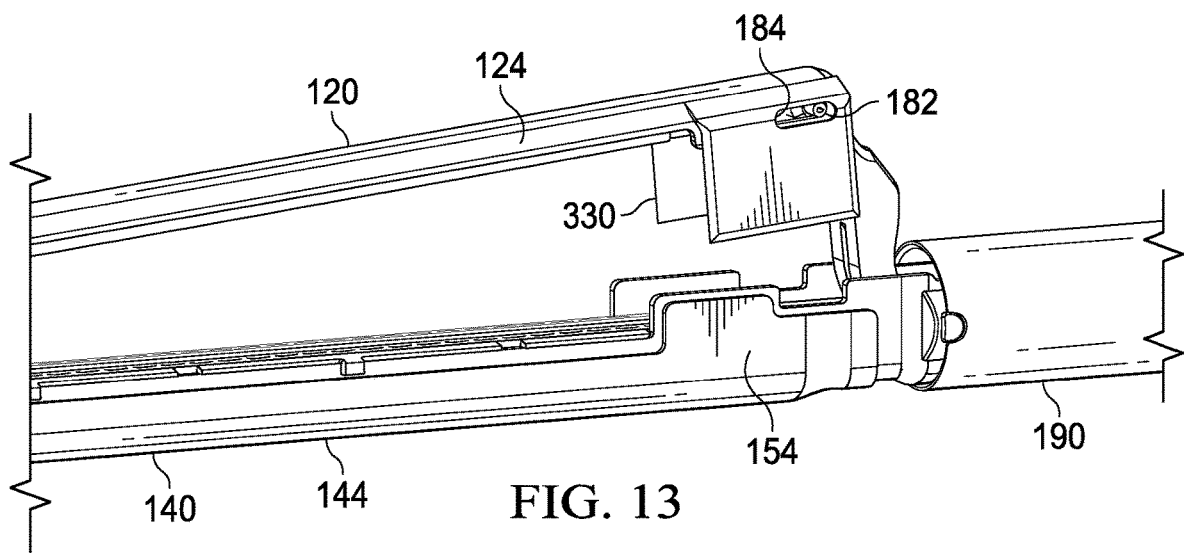
FIG. 13 depicts the stapler of FIG. 1A, where the jaws of the stapler are shown in an open position and wherein a tissue-blocking anvil cap has been formed or placed on the upper jaw of the stapler.

FIG. 12 depicts end effector 100, wherein the jaws of end effector 100 are shown in a closed position and wherein tissue-blocking anvil cap 330 has been formed or placed on upper jaw 120 of end effector 100. FIG. 13 depicts end effector 100, wherein the jaws of end effector 100 are shown in an open position and wherein tissue-blocking anvil cap 330 has been formed or placed on upper jaw 120 of end effector 100. In this implementation, anvil cap 300 may be formed on anvil frame 124 or may be rigidly attached thereto as a separate structure using welding, adhesives, or attachment hardware such as bolts or screws. Anvil cap 330 cooperates with second proximal tissue stop 154 on cartridge frame 144 to create a shield for preventing tissue from entering no tissue zone 160. When upper and lower jaws 120 and 140 are closed, anvil cap 330 may not protrude past the bottom edge of cartridge frame 144. When upper and lower jaws 120 and 140 are open, anvil cap 330 can shield the no tissue zone.

Figure 14:
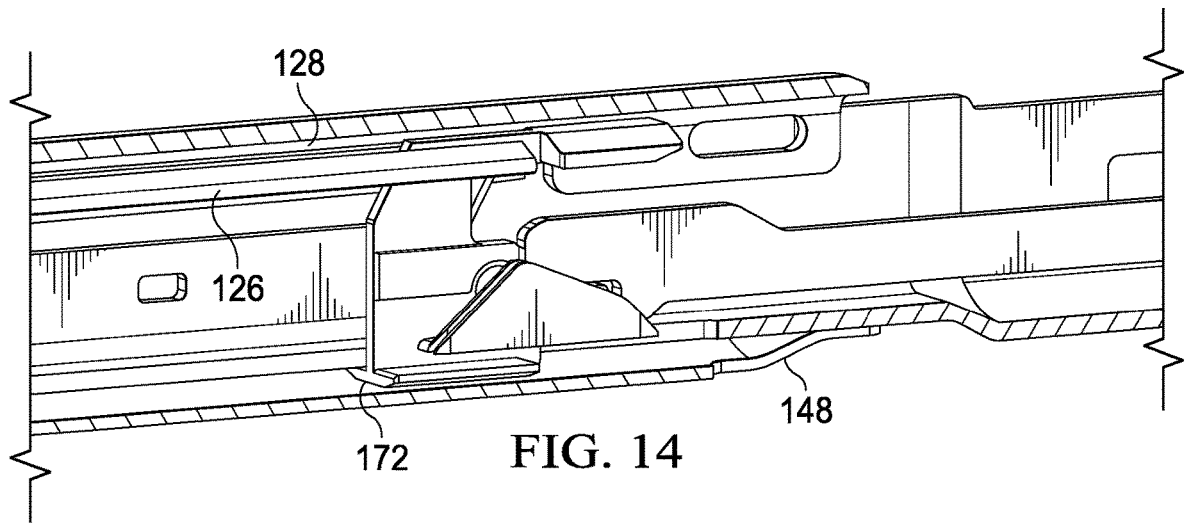
FIG. 14 depicts an implementation that prevents the transection of tissue without closure thereof with surgical staples through the use of a cantilever beam.

FIG. 14 depicts an implementation that prevents the transection of unstapled tissue. This implementation is referred to as the "cantilever beam" and includes disengaging I-beam knife 172. In FIG. 14, I-Beam knife 172 is shown as a cantilevered beam knife. In this implementation, the feature responsible for clamping down anvil plate 126 is set in front of knife 172, which transects the tissue. In this way, knife 172 cannot cut tissue without the tissue already being fastened with staples because the cantilever beam escapes anvil assembly 122 before knife 172, allowing end effector jaws 120 and 140 to be opened when knife 172 is in the proximal position. In this implementation, if tissue is present in the no tissue zone, the tissue may be stapled but will not be cut.

FIG. 15 depicts an implementation that utilizes a reversing knife approach to preventing the transection of unstapled tissue through the inclusion of a secondary thread on the primary firing screw. Formed along most of the length of firing screw 500 is a primary coarse thread 502 that provides enough travel to drive firing nut 504 from the distal end of end effector 100 to the proximal end thereof, cutting and firing staples longitudinally along the end effector. On the proximal end of firing screw 500 secondary thread segment 506 is formed having thread 506, which is finer that primary thread 502. The pitch and travel of secondary thread 506 are proportional to primary thread 502. Firing nut 504 rides along primary coarse thread 502 only and limit switch nut 508 rides along secondary fine thread 506 only. When firing screw 500 is turning, firing nut 504 and limit switch nut 508 move in the same direction but at different linear velocities and therefore travel different distances. Limit switch nut 508 will travel in between two limit switches, distal limit switch 510 and proximal limit switch 512 (see FIG. 15). Before end effector 100 is fired, firing nut 504 will be at the distal end of the end effector and limit switch nut 508 will be activating distal limit switch 510. After end effector 100 has fired, firing nut 504 will be at the proximal end of the end effector and limit switch nut 508 will be activating proximal limit switch 512.

FIG. 16 depicts an implementation that utilizes a reversing knife approach to preventing the transection of unstapled tissue through the inclusion of a secondary fine thread on an auxiliary firing screw. This implementation is similar to what shown in FIG. 15; however, auxiliary firing screw 514 obtains its rotation from firing screw 502 by way of meshed gears 516 and 518. In either implementation, primary firing screw 500 or auxiliary firing screw 514 may be any combination of left-handed or right-handed threads.

Figure 17:
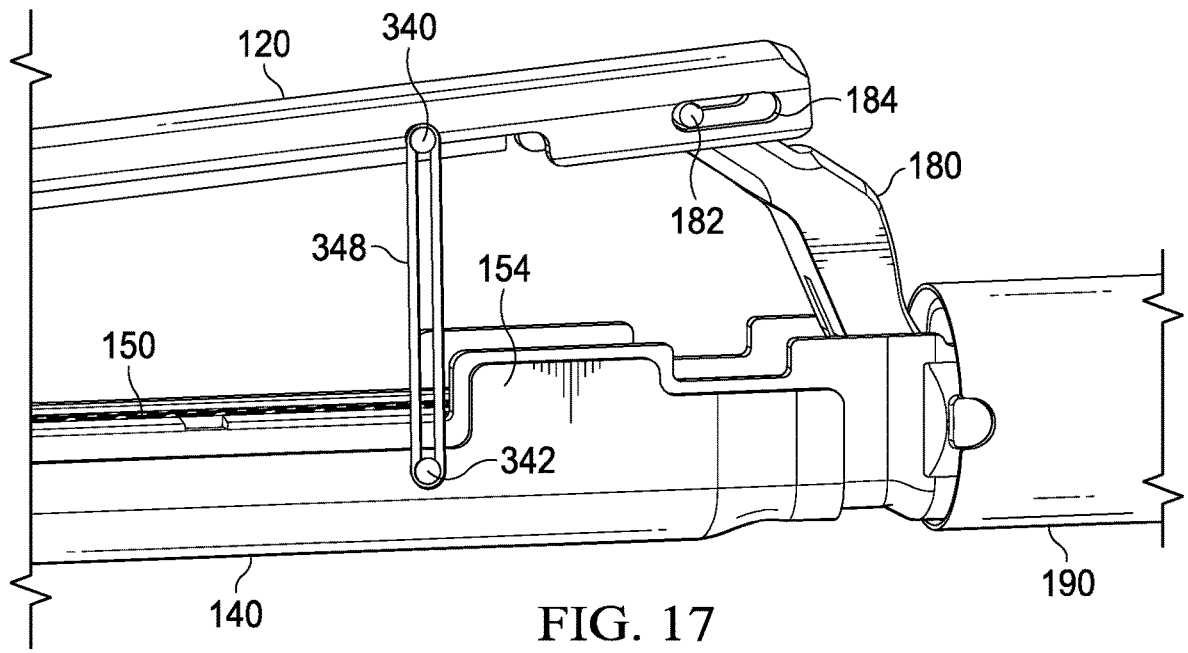
FIG. 17 depicts the stapler of FIG. 1A, where the jaws of the stapler are shown in an open position and where a tissue-blocking elastomeric band has been mounted on an attachment screw on the upper jaw and an attachment screw on the lower jaw.
Figure 18:
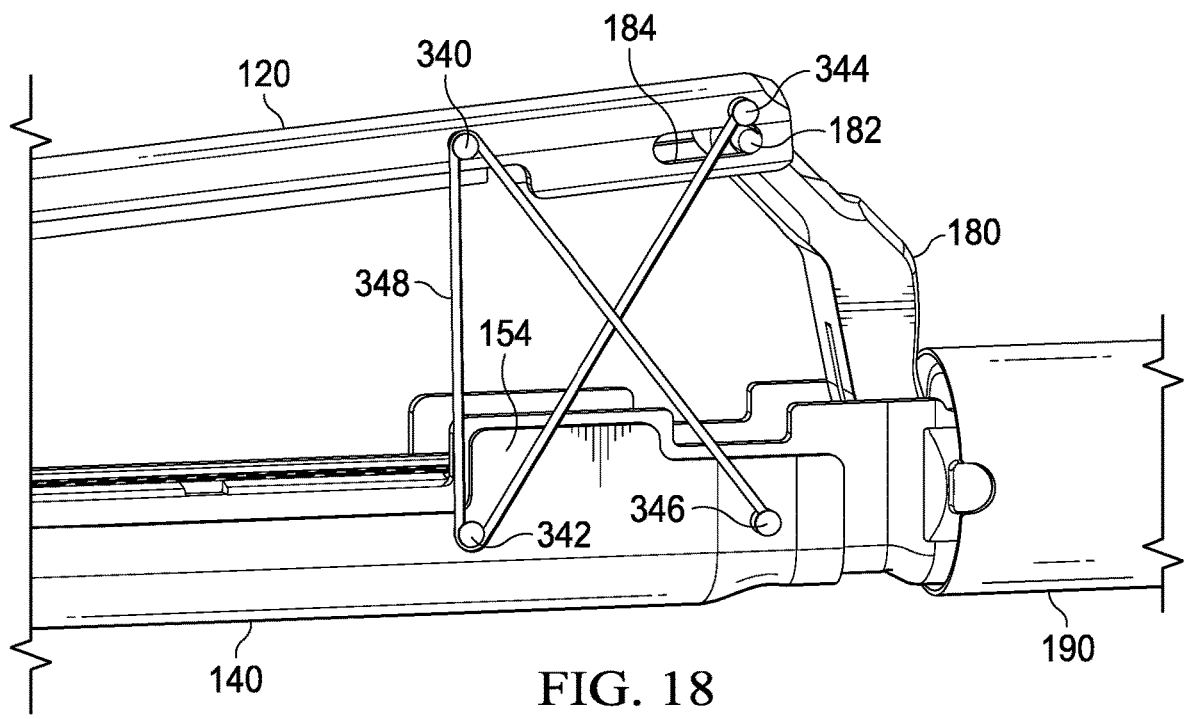
FIG. 18 depicts the stapler of FIG. 1A, wherein the jaws of the stapler are shown in an open position and wherein a tissue-blocking elastomeric band has been mounted on two attachment screws on the upper jaw and two attachment screws on the lower jaw in a crossed configuration.
Figure 19:
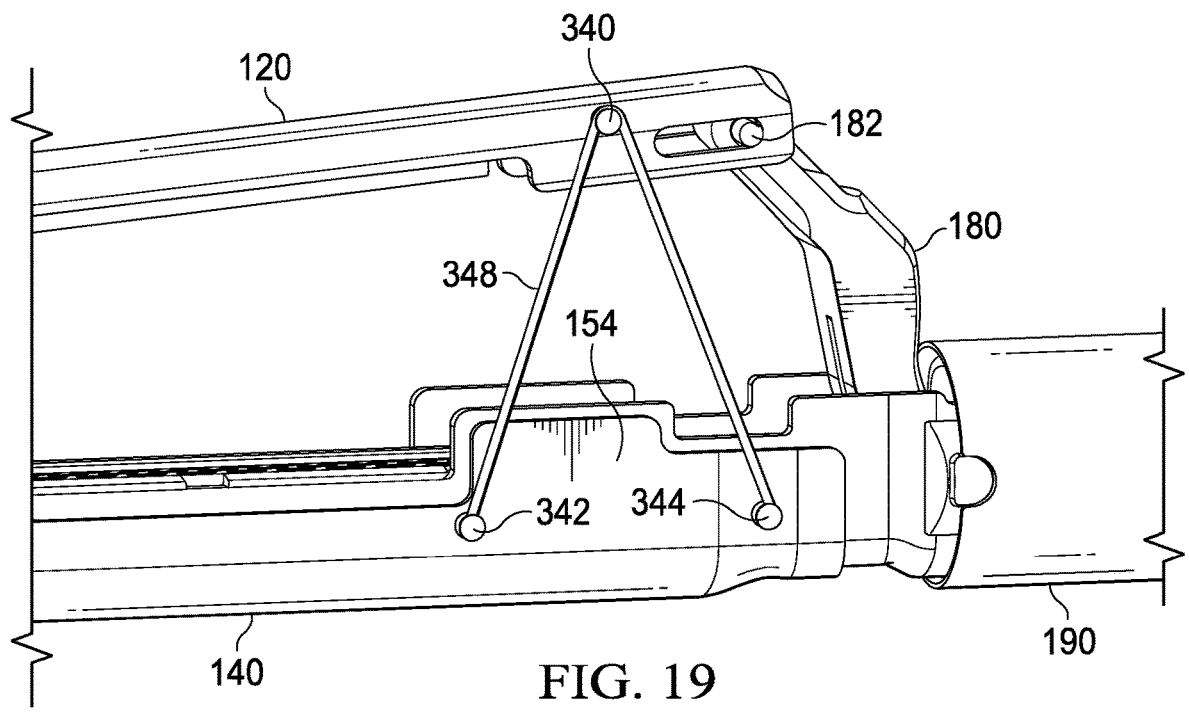
FIG. 19 depicts the stapler of FIG. 1A, wherein the jaws of the stapler are shown in an open position and wherein a tissue-blocking elastomeric band has been mounted an attachment screw on the upper jaw and two attachment screws on the lower jaw in a triangular configuration.

FIG. 17 depicts an implementation of end effector 100, wherein the jaws of end effector 100 are shown in an open position and where tissue-blocking elastomeric band 348 has been mounted on attachment screw 340 on upper jaw 120 and attachment screw 342 on lower jaw 140. FIG. 18 depicts end effector 100, where the jaws of end effector 100 are shown in an open position and where tissue-blocking elastomeric band 348 has been mounted on attachment screws 340 and 344 on upper jaw 120 and attachment screws 342 and 346 on lower jaw 140 in a crossed configuration. FIG. 19 depicts end effector 100, wherein the jaws of end effector 100 are shown in an open position and where tissue-blocking elastomeric band 348 has been mounted on attachment screw 340 on upper jaw 120 and attachment screws 342 and 344 on lower jaw 140 in a triangular configuration. Elastic band 348 may be silicone, urethane, or similar material, and may be a full loop or an elastic string. In alternate implementations, the attachments screws are replaced with rivets, glued posts, welded posts, or stamped or molded features formed on upper and lower jaws 120 and 140.

Figure 20:
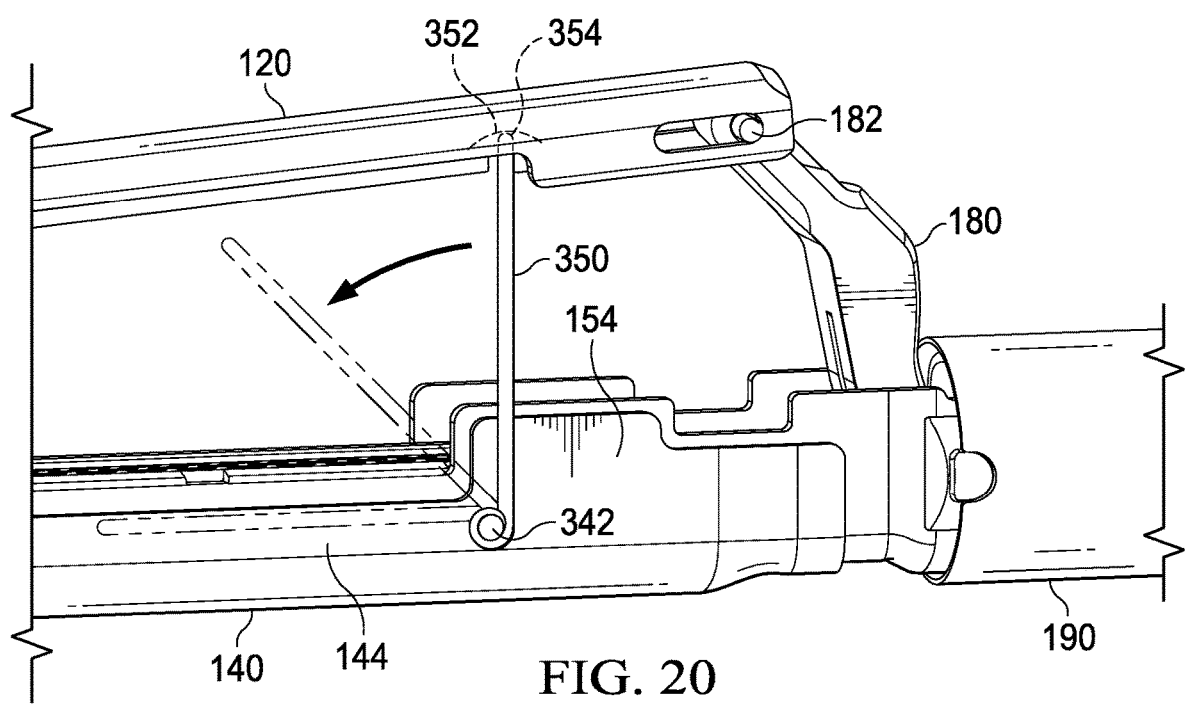
FIG. 20 depicts the stapler of FIG. 1A, wherein the jaws of the stapler are shown in an open position and wherein a tissue-blocking rotating post has been positioned between the upper and lower jaws of the stapler.

FIG. 20 depicts an implementation of end effector 100, where the jaws of end effector 100 are shown in an open position and wherein tissue-blocking rotating post 350 has been positioned between upper and lower jaws 120 and 140 of end effector 100. In the implementation shown in FIG. 20, attachment point 342 includes a torsional spring that biases post 350 in a vertical position. When jaws 120 and 140 are open, the torsional spring rotates post 350 upward, perpendicular to cartridge frame 144. When jaws 120 and 140 close, a moment is applied to post attachment point 342 by way of anvil frame 124 on the end of post 350 that counteracts the force on the torsional spring and rotates post 350 counterclockwise or clockwise until post 350 is parallel, or nearly parallel, to cartridge frame 144. FIG. 20 also depicts an alternate configuration, wherein the end of post 350 opposite attachment point 342 is constrained by cam profile 352 on anvil frame 124, and wherein the end of post 350 opposite attachment point 342 acts as cam follower 354. As jaws 120 and 140 open, cam profile 352 forces cam follower 354 into a vertical position, perpendicular to cartridge frame 144. As jaws 120 and 140 close, cam profile 352 forces cam follower 354 into a horizontal position, parallel, or nearly parallel, to cartridge frame 144. This implementation may include any combination of a torsional spring, and cam profile and cam follower.

Figure 21:
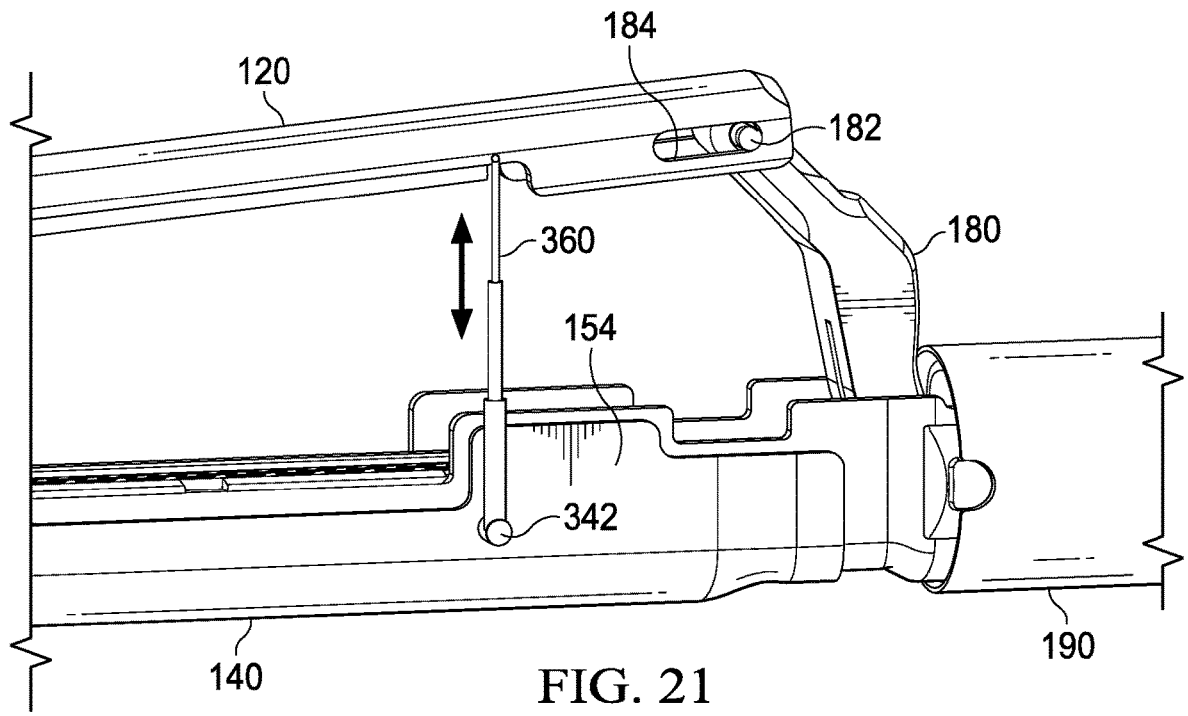
FIG. 21 depicts the stapler of FIG. 1A, wherein the jaws of the stapler are shown in an open position and where a tissue-blocking telescoping post has been positioned between the upper and lower jaws of the stapler.

FIG. 21 depicts an implementation of end effector 100, wherein the jaws of end effector 100 are shown in an open position and wherein tissue-blocking telescoping post 360 has been positioned between upper and lower jaws 120 and 140 of end effector 100. In the implementation shown in FIG. 21, post 360 does not rotate but telescopically translates in a vertical manner. Telescoping post 360 may be biased upward using a compression spring that is compressed when jaws 120 and 140 close. When jaws 120 and 140 open, the compression spring forces the inner telescopic members of post 360 upward. A structure such as, for example, a ball and socket joint, may be included on anvil frame 124 for constraining the lateral movement of telescoping post 360 and providing a surface for compressing post 360. This structure or feature may be attached to anvil frame 124 using screws, rivets, glue, welding, or by using features stamped or molded into anvil frame 124.

Figure 22:
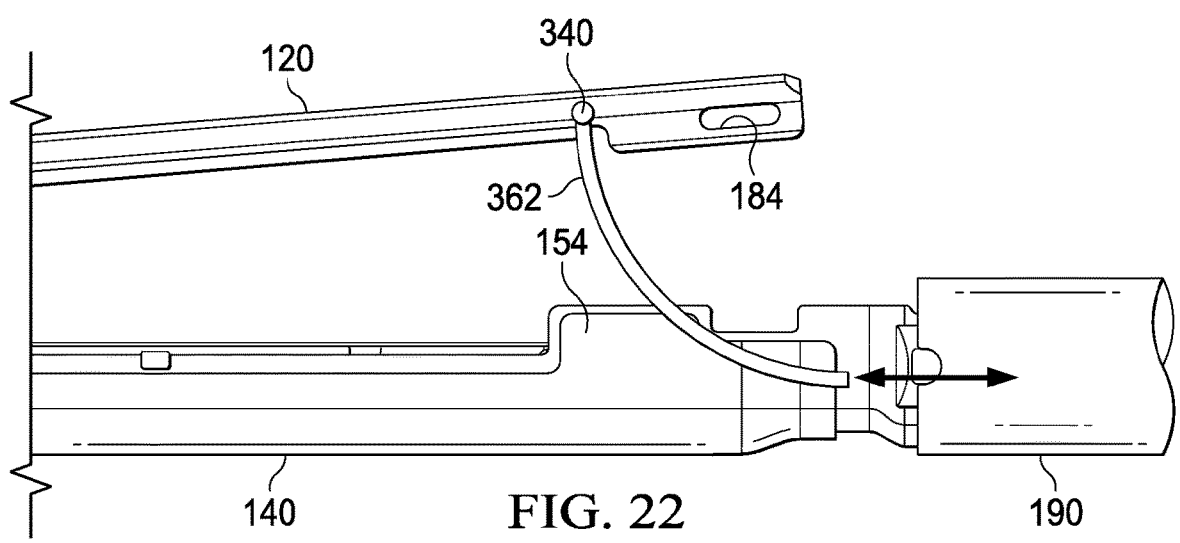
FIG. 22 depicts the stapler of FIG. 1A, wherein the jaws of the stapler are shown in an open position and where a tissue-blocking curved linkage has been positioned between the upper and lower jaws of the stapler.

FIG. 22 depicts an implementation of end effector 100, where the jaws of end effector 100 are shown in an open position and wherein tissue-blocking curved linkage 362 has been positioned between upper and lower jaws 120 and 140 of end effector 100. In the implementation shown in FIG. 22, curved linkage 362 is used to clamp upper jaw 120 to lower jaw 140. Curved linkage 362 is pinned in anvil frame 124 wherein it rotates freely. Curved linkage 362 pivots or slides near cartridge 150 as it is pushed or pulled from inside support tube 190 to open or close jaws 120 and 140. Curved linkage 362 is present inside the no tissue zone, thereby shielding tissue from entering it, and is bowed to allow adjacent tissue in jaws 120 and 140 to be pushed out of the no tissue zone.

Figure 23:
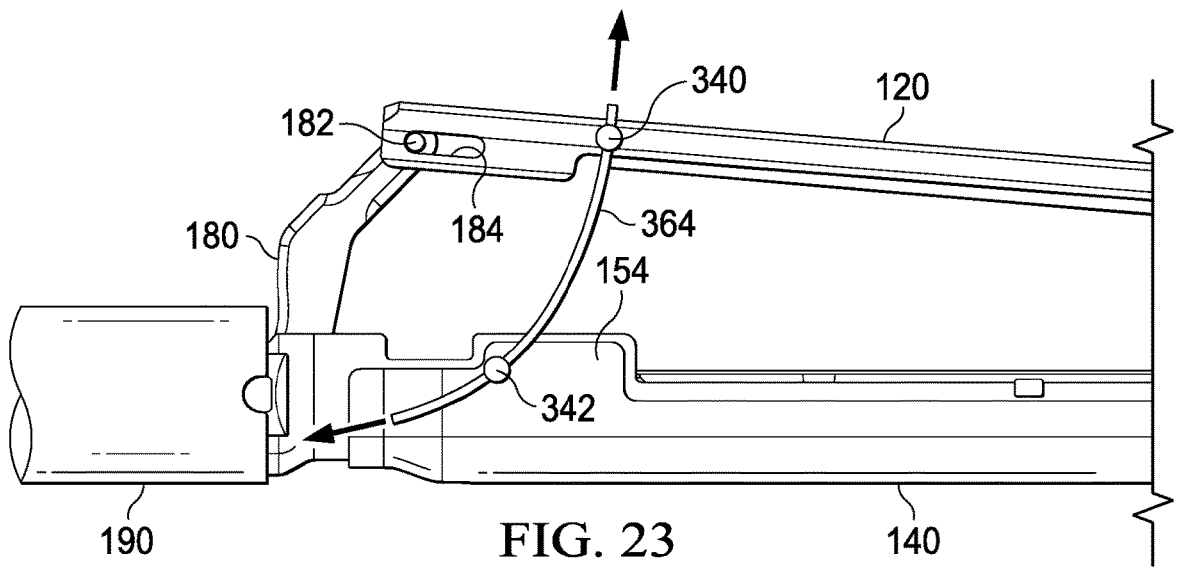
FIG. 23 depicts the stapler of FIG. 1A, wherein the jaws of the stapler are shown in an open position and where a tissue-blocking passive curved linkage has been positioned between the upper and lower jaws of the stapler.

FIG. 23 depicts an implementation of end effector 100, where the jaws of end effector 100 are shown in an open position and wherein tissue-blocking passive curved linkage 362 has been positioned between upper and lower jaws 120 and 140 of end effector 100. In the implementation shown in FIG. 23, curved linkage 364 includes a passive band that cooperates with a separate linkage. The band is pinned on upper jaw 120 at 340 and pivots in lower jaw 140 at pivot point 342. The passive band does not mechanically clamp jaws 120 and 140 together but shields the no tissue zone. The passive band is pulled underneath the separate link when jaws 120 and 140 are closed. When jaws 120 and 140 are opened, the passive band is bowed and present in the no tissue zone.

Figure 24:
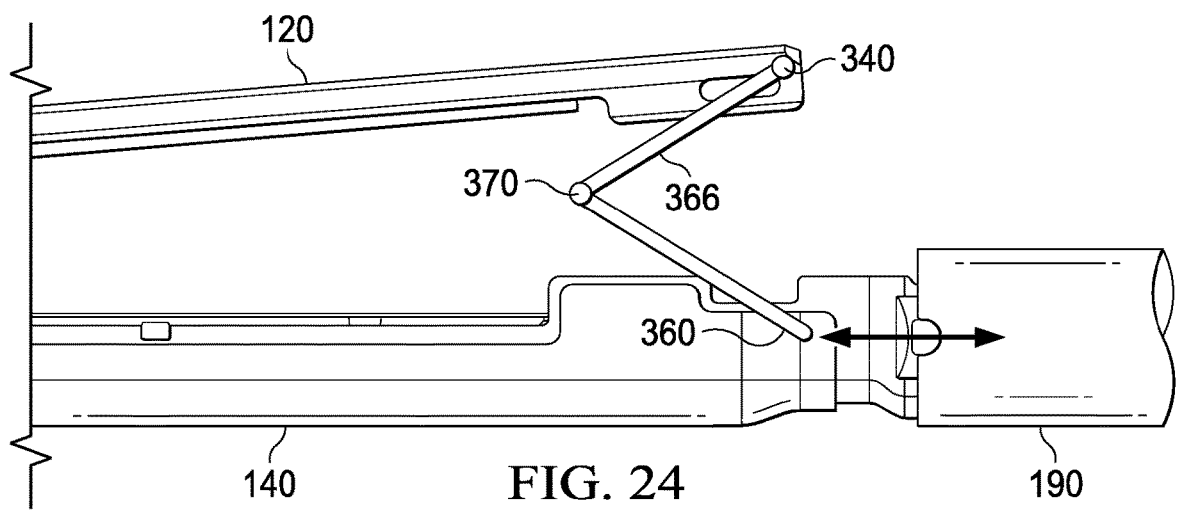
FIG. 24 depicts the stapler of FIG. 1A, wherein the jaws of the stapler are shown in an open position and where a tissue-blocking pivoting double linkage has been positioned between the upper and lower jaws of the stapler.

FIG. 24 depicts an implementation of end effector 100, where the jaws of end effector 100 are shown in an open position and where a tissue-blocking pivoting double linkage 365 has been positioned between upper and lower jaws 120 and 140 of end effector 100. Double linkage 365, which has an additional degree of freedom compared to other disclosed implementations, includes first link 366 connected to second link 370 at pivot point 370. When jaws 120 and 140 are closing, pivot point 370 pushes tissue out of the no tissue zone, if present, and double linkage 365 then folds into cartridge frame 144. When jaws 120 and 140 are opening, the double linkage unfolds and becomes a rigid member that shields the no tissue zone. Double linkage 365 is connected to anvil frame 124 in a hinged manner at attachment point 340.

Figure 25:
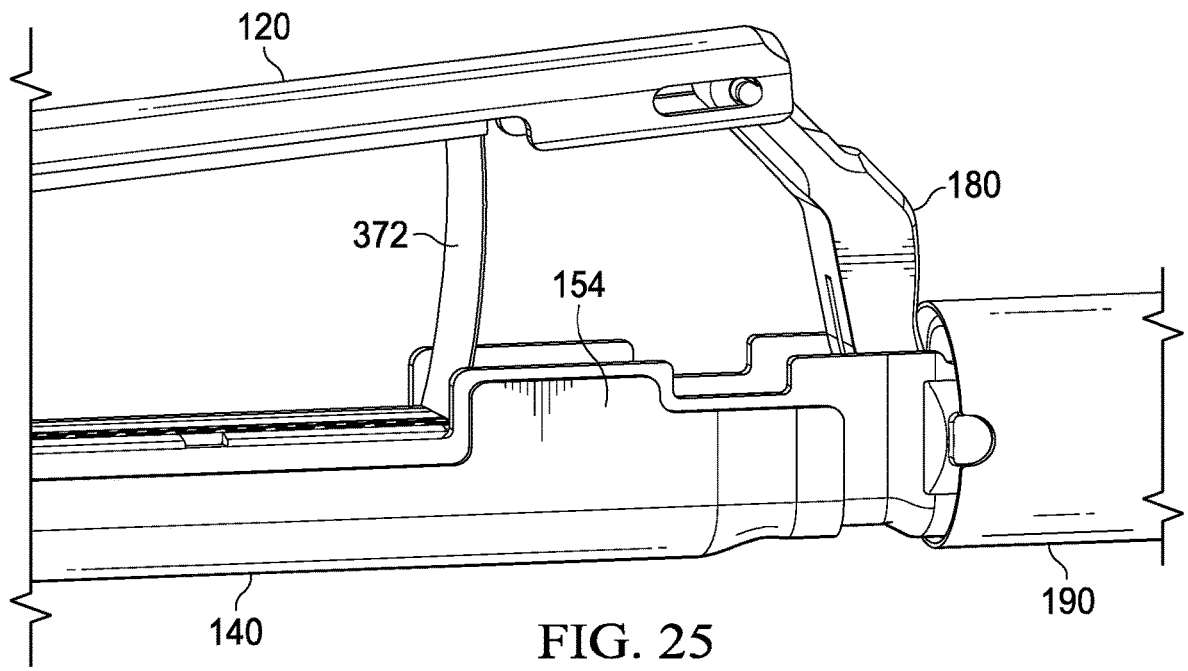
FIG. 25 depicts the stapler of FIG. 1A, wherein the jaws of the stapler are shown in an open position and where a tissue-blocking sacrificial cut band has been positioned between the upper and lower jaws of the stapler.

FIG. 25 depicts an implementation of end effector 100, wherein the jaws of end effector 100 are shown in an open position and where a tissue-blocking sacrificial cut band 372 has been positioned between upper and lower jaws 120 and 140 of end effector 100. In the implementation shown in FIG. 25, sacrificial cut band 372 occupies the entire distance between upper and lower jaws 120 and 140 and the entire width of both cartridge frame 144 and anvil frame 124. Sacrificial cut band 372 is cut or destroyed when I-Beam knife 172 fires through the band at the end of the firing stroke of knife 172. The sacrificial band is typically made from a soft material, such as silicone, urethane, or any other suitable material, so that knife 172 can effectively fire through the band. The band shields tissue from the no tissue zone while also allowing the jaws of the end effector device to close.

Figure 26:
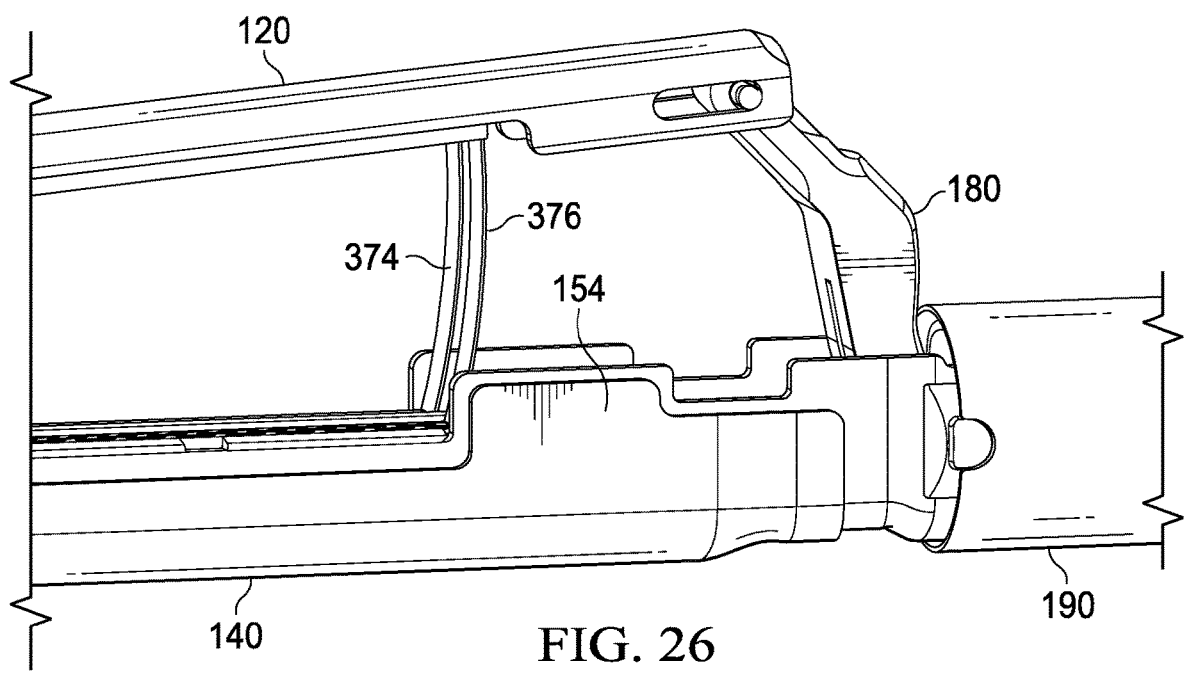
FIG. 26 depicts the stapler of FIG. 1A, wherein the jaws of the stapler are shown in an open position and wherein a tissue-blocking split band has been positioned between the upper and lower jaws of the stapler.

FIG. 26 depicts an implementation of end effector 100, where the jaws of end effector 100 are shown in an open position and wherein a tissue-blocking split band 373 has been positioned between upper and lower jaws 120 and 140 of end effector 100. In the implementation shown in FIG. 26, split band 373 includes first band portion 374 and separate second band portion 376 for allowing I-Beam knife 172 to pass through the separate band portions when fired. Split band 373 may be attached to cartridge frame 144 or cartridge 150 on lower jaw 140 and to anvil frame 124 on upper jaw 120. Split band 373 shields tissue from the no tissue zone while also allowing the jaws of the end effector device to close.

Figure 27:
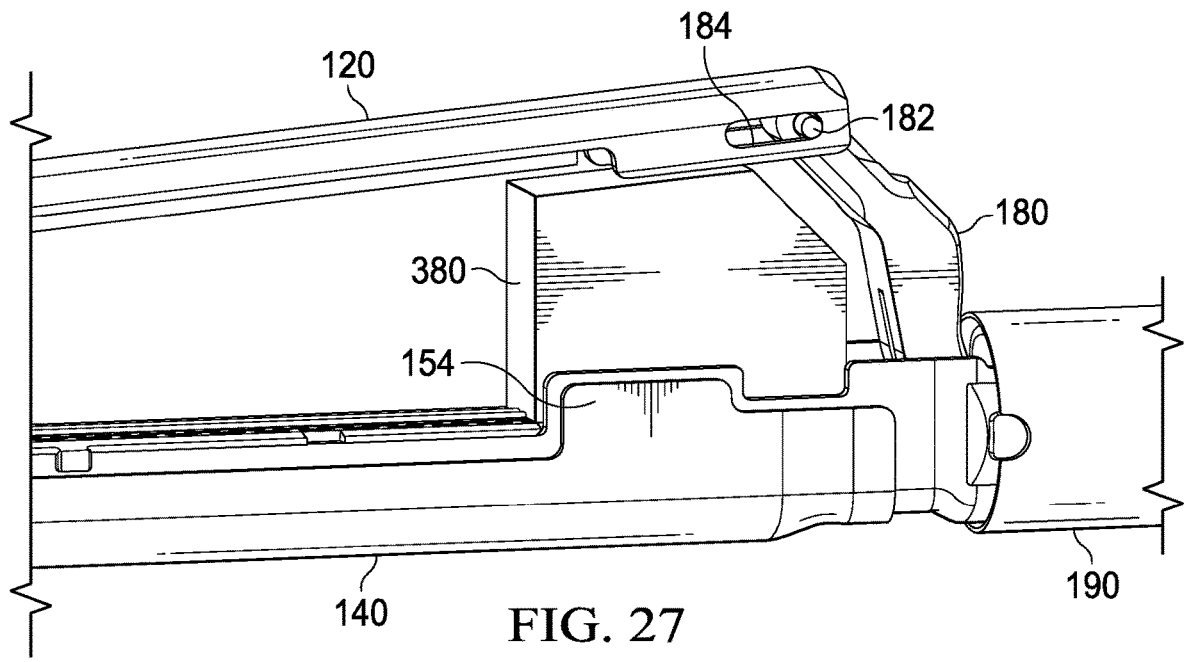
FIG. 27 depicts the stapler of FIG. 1A, wherein the jaws of the stapler are shown in an open position and wherein a tissue-blocking compliant sacrificial foam block has been positioned between the upper and lower jaws of the stapler.
Figure 28:
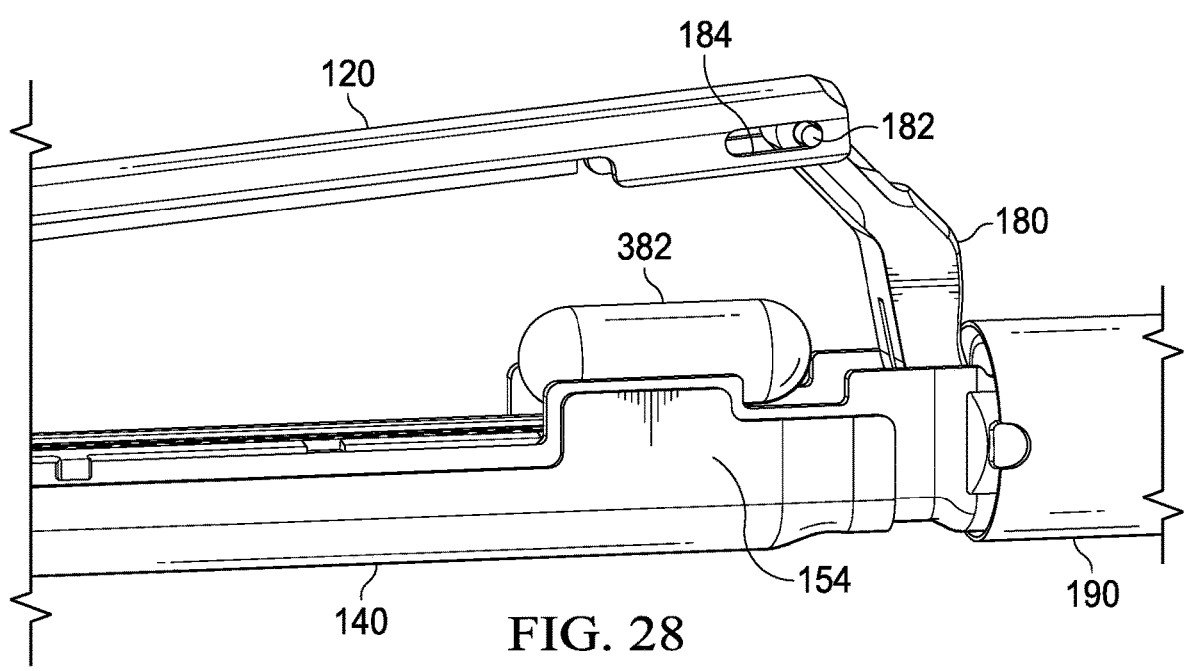
FIG. 28 depicts the stapler of FIG. 1A, wherein the jaws of the stapler are shown in an open position and wherein a tissue-blocking compliant sacrificial balloon has been positioned between the upper and lower jaws of the stapler.

FIG. 27 depicts an implementation of end effector 100, wherein the jaws of end effector 100 are shown in an open position and where tissue-blocking compliant sacrificial foam block 380 has been positioned between upper and lower jaws 120 and 140 of end effector 100. FIG. 28 depicts an implementation of end effector 100, where the jaws of end effector 100 are shown in an open position and wherein tissue-blocking compliant sacrificial balloon 382 has been positioned between upper and lower jaws 120 and 140 of end effector 100. Both compliant sacrificial foam block 380 and compliant sacrificial balloon 382 can permit I-beam knife 172 to pass through the area of end effector 100 occupied by these elements or features. Compliant sacrificial foam block 380 may be attached to anvil frame 124, cartridge frame 144, cartridge 150, or may be simply constrained by the components surrounding the no tissue zone. The block is compliant, in an example, and may be fabricated from an open cell foam or closed cell foam, and allows upper and lower jaws 120 and 140 to clamp together. The block can include a specific density that allows I-Beam knife 172 to fire through it when compressed. The compliant block may be sacrificial and may be destroyed from the firing sequence of end effector 100. Compliant sacrificial balloon 382 can be a gas filled compliant balloon, rather than a block, that allows upper and lower jaws 120 and 140 to clamp together without bursting and may be destroyed from the firing sequence of end effector 100. The compliant balloon may be attached to anvil frame 124, cartridge frame 144, cartridge 150, or may be simply constrained by the components surrounding the no tissue zone.

Figure 29:
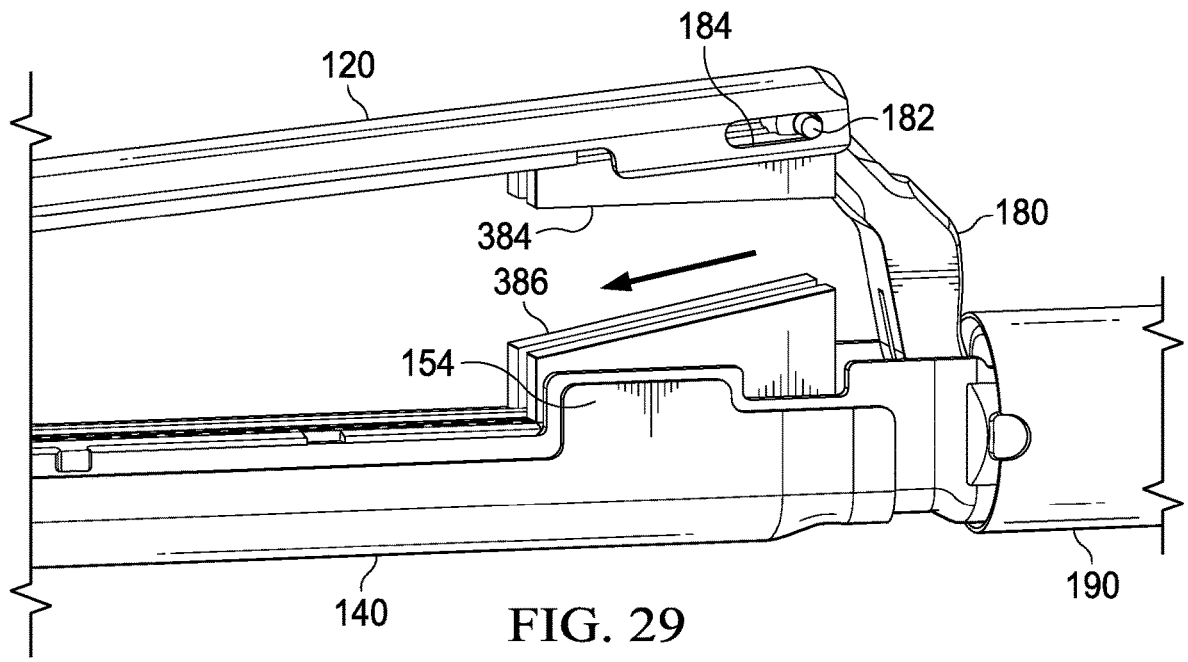
FIG. 29 depicts the stapler of FIG. 1A, wherein the jaws of the stapler are shown in an open position and wherein a zero-clearance block has been positioned between the upper and lower jaws of the stapler.

FIG. 29 depicts an implementation of end effector 100, wherein the jaws of end effector 100 are shown in an open position and wherein tissue-blocking zero clearance block 383 having top portion 384 and bottom portion 386 has been positioned between upper and lower jaws 120 and 140 of end effector 100. In the implementation shown in FIG. 29, zero clearance block 383 is neither compliant nor sacrificial, but rather is a rigid tapered block attached to both upper and lower jaws 120 and 140 that pushes clamped tissue out of the no tissue zone. Both top portion 384 and bottom portion 386 can include a centrally placed channel or gap that permits I-beam knife 172 to travel through each portion. Rigid tapered block 383 may be a structure integrated into anvil frame 124 and cartridge frame 144 (or cartridge 150) or it may be a separate component fabricated from rigid plastic such as nylon or from metal such as stainless steel. If the rigid tapered block is a separate component, it may be attached to upper and lower jaws 120 and 140 by gluing, welding, snap features, or with hardware such as bolts or screws. The rigid block may produce zero clearance in the no tissue zone when the jaws of end effector 100 are closed.

Figure 30:
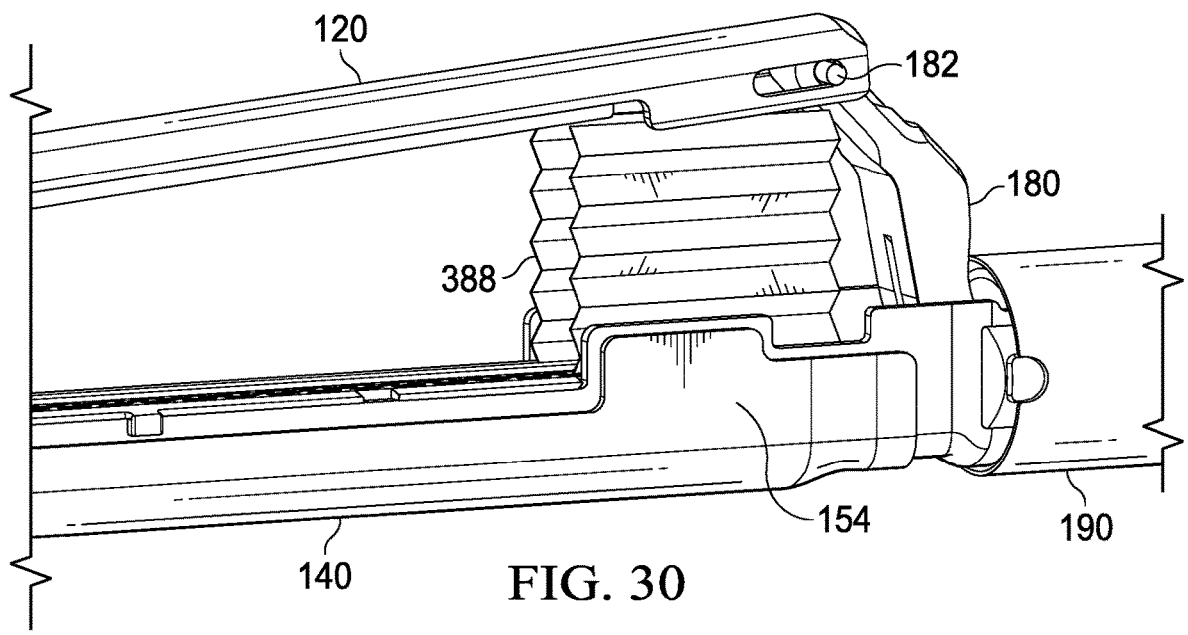
FIG. 30 depicts the stapler of FIG. 1A, wherein the jaws of the stapler are shown in an open position and wherein an accordion-like tissue blocking device has been positioned between the upper and lower jaws of the stapler.
Figure 31:
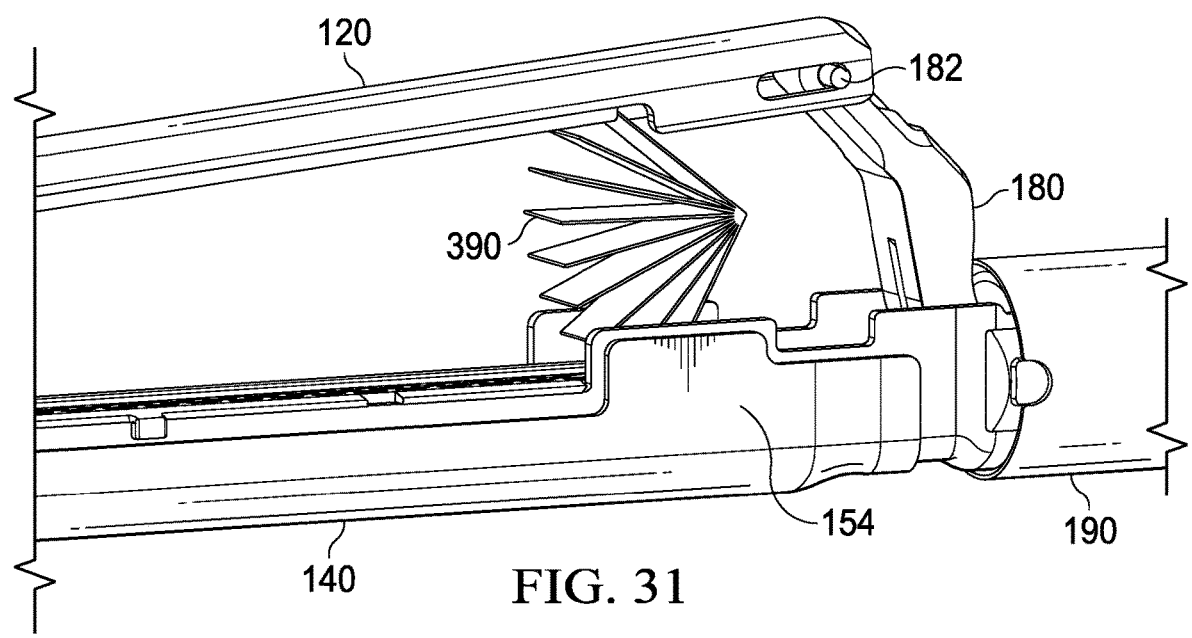
FIG. 31 depicts the stapler of FIG. 1A, wherein the jaws of the stapler are shown in an open position and wherein an alternate accordion-like tissue blocking device has been positioned between the upper and lower jaws of the stapler.

FIGS. 30 and 31 depict alternate devices and methods of shielding the no tissue zone by using an accordion-like shield that can "fan out" when the jaws of the end effector are open and "fold in" when the jaws of the end effector are closed. Example devices can be attached to upper and lower jaws 120 and 140 to give the shield two or more anchor points when pulled apart. These accordion-like devices may be fabricated from a rigid or flexible metal or plastic or any other suitable material. FIG. 30 depicts an implementation of end effector 100, where the jaws of end effector 100 are shown in an open position and where accordion shield 388 has been positioned between upper and lower jaws 120 and 140 of end effector 100. Accordion shield 388 extends along each side of the no tissue zone and maintains its overall footprint when extended. In this implementation, I-Beam knife 172 can travel in-between the two sides of the accordion shield. FIG. 31 depicts an implementation of end effector 100, where the jaws of end effector 100 are shown in an open position and where fan shield 390 has been positioned between upper and lower jaws 120 and 140 of end effector 100. In the implementation shown in FIG. 31, fan shield 390 fans out distally when extended and extends in a semi-circular pattern from a central axis inside the no tissue zone. Fan shield 390 may be sacrificial, destroyed by knife 172 during the firing sequence of end effector 100, or it may be split into two separate fans to allow knife 172 to pass through the no tissue zone.

Figure 32:
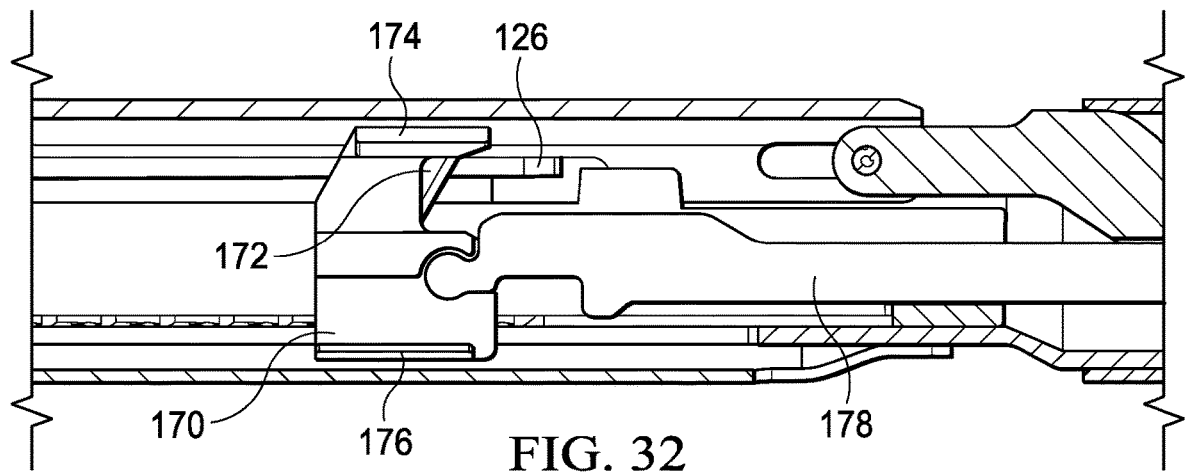
FIG. 32 depicts an implementation that utilizes disengaging I-beam knife approach (normal orientation) to prevent the transection of tissue without the closure thereof with surgical staples.
Figure 33:
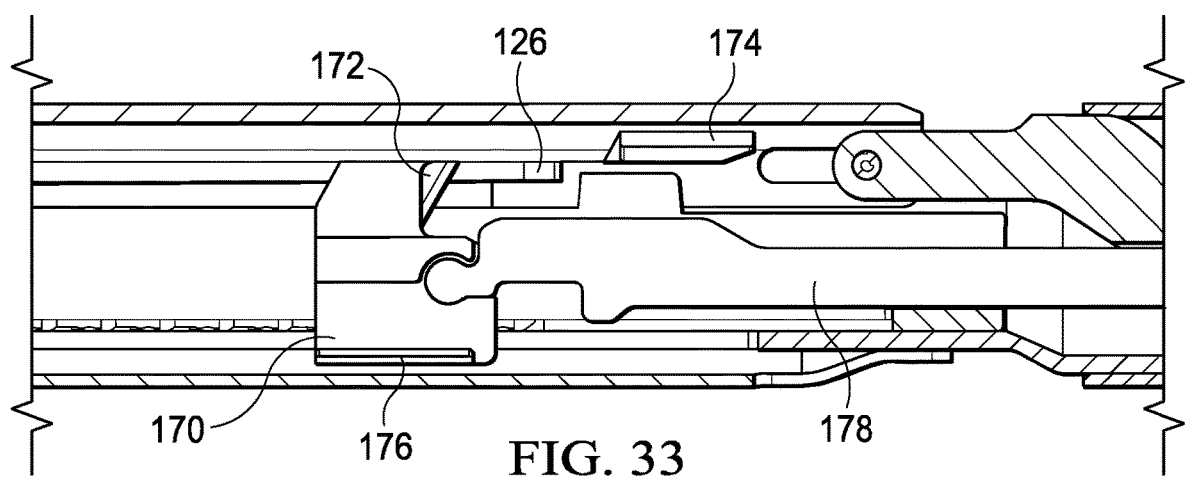
FIG. 33 depicts an implementation that utilizes a disengaging I-beam knife approach, shown in a disengaged orientation, to prevent the transection of tissue without the closure thereof with surgical staples.

FIG. 32 depicts an implementation that utilizes a disengaging I-beam knife approach (normal orientation) to prevent the transection of unstapled tissue and FIG. 33 depicts an implementation that utilizes a disengaging I-beam knife approach (disengage orientation) to prevent the transection of unstapled tissue. In the implementations shown in FIGS. 32 and 33, I-beam top shelf 174 can be disengaged from anvil plate 126 at proximal tissue stop 154. In these implementations, knife 172 stops at proximal tissue stop 154 or in front of the no tissue zone, but I-beam top shelf 174 may continue on a separate linear travel mechanism until it clears anvil plate 126 as shown in FIG. 33. Alternately, I-beam top shelf 174 may become free from I-Beam 170 by means of a mechanical fuse or the like, thereby allowing upper jaw 120 to open relative to lower jaw 140. In a similar fashion, I-beam bottom shelf 176 may be disengaged. I-beam top shelf 174 may be disengaged from anvil frame 124 and I-beam bottom shelf 176 may become disengaged from cartridge frame 144 by a trap door or a moving door mechanism, allowing the end effector jaws to open without being constrained by the top and/or bottom shelf.

Figure 34:
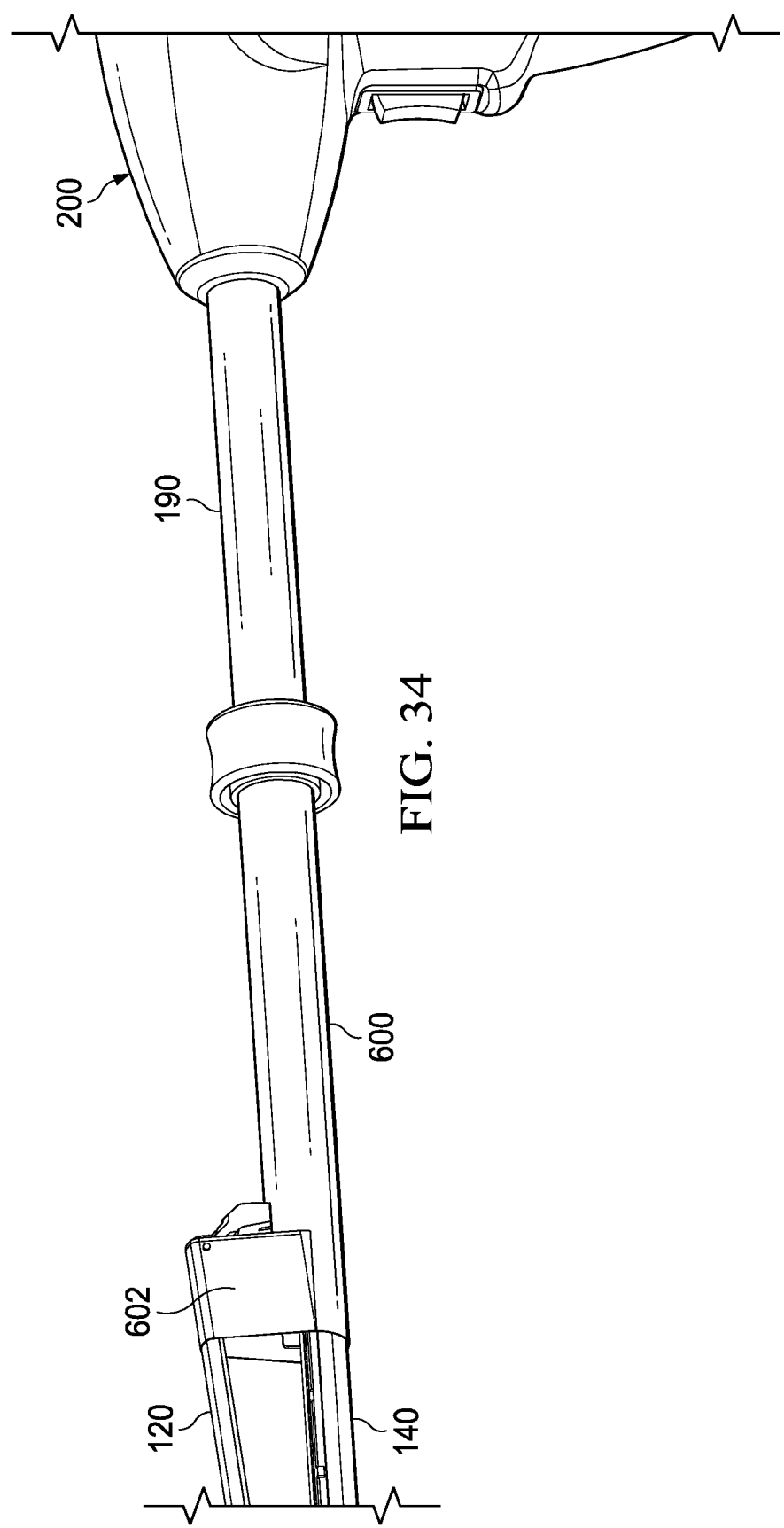
FIG. 34 depicts an implementation that utilizes an external device or introducer sheath to shield a no tissue zone.

FIG. 34 depicts an implementation that utilizes an external device referred to as an introducer sheath to shield the no tissue zone. In the implementation shown in FIG. 34, introducer sheath 600 is not fixed to end effector 100, but slides longitudinally along the stapling instrument and may be concentric to the end effector 100. Introducer sheath 600 may cooperate with a trocar, a shielding sheath, or another device. Shielding sheath 602 may be flexible in the no tissue zone location, allowing the end effector jaws to open, close, and fit through a trocar while still shielding the no tissue zone.

All literature and similar material cited in this application, including, but not limited to, patents, patent applications, articles, books, treatises, and web pages, regardless of the format of such literature and similar materials, are expressly incorporated by reference in their entirety. Should one or more of the incorporated references and similar materials differs from or contradicts this application, including but not limited to defined terms, term usage, described techniques, or the like, this application controls.

As previously stated and as used herein, the singular forms "a," "an," and "the" refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particular suitable methods and materials are described herein. Unless context indicates otherwise, the recitations of numerical ranges by endpoints include all numbers subsumed within that range. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this specification are used to describe and account for small fluctuations, such as due to variations in processing. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%, and/or 0%.

Underlined and/or italicized headings and subheadings are used for convenience only, do not limit the disclosed subject matter, and are not referred to in connection with the interpretation of the description of the disclosed subject matter. All structural and functional equivalents to the elements of the various implementations described throughout this disclosure that are known or later come to be known to those of ordinary skill in the art are expressly incorporated herein by reference and intended to be encompassed by the disclosed subject matter. Moreover, nothing disclosed herein is intended to be dedicated to the public regardless of whether such disclosure is explicitly recited in the above description.

There may be many alternate ways to implement the disclosed inventive subject matter. Various functions and elements described herein may be partitioned differently from those shown without departing from the scope of the disclosed inventive subject matter. Generic principles defined herein may be applied to other implementations. Different numbers of a given module or unit may be employed, a different type or types of a given module or unit may be employed, a given module or unit may be added, or a given module or unit may be omitted.

It should be appreciated that all combinations of the foregoing concepts and additional concepts discussed in greater detail herein (provided such concepts are not mutually inconsistent) are contemplated as being part of the disclosed inventive subject matter. In particular, all combinations of claimed subject matter appearing at the end of this disclosure are contemplated as being part of the inventive subject matter disclosed herein. While the disclosed inventive subject matter has been illustrated by the description of example implementations, and while the example implementations have been described in certain detail, there is no intention to restrict or in any way limit the scope of the appended claims to such detail. Additional advantages and modifications will readily appear to those skilled in the art. Therefore, the disclosed inventive subject matter in its broader aspects is not limited to any of the specific details, representative devices and methods, and/or illustrative examples shown and described. Accordingly, departures may be made from such details without departing from the spirit or scope of the general inventive concept.

What is claimed is:

1. A system for preventing unwanted tissue migration in surgical staplers, comprising:
   (a) a surgical stapler having an end effector for dispensing surgical staples, wherein the end effector includes:
      (i) an upper jaw the upper jaw including a proximal end and a distal end;
      (ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
      (iii) a first tissue stop formed on the distal end of the lower jaw;
      (iv) a second tissue stop formed on the proximal end of the of the lower jaw, wherein the second tissue stop and the proximal end of the upper jaw define a no tissue zone when the surgical stapler is in an open position; and
      (v) a tissue cutting device disposed within the lower jaw for resecting tissue; and
   (b) a warning, blocking, impeding, or barrier forming device for preventing the unwanted migration of tissue into the no tissue zone during surgical procedures such that resection of unstapled tissue is prevented, wherein the warning, blocking, impeding, or barrier forming device includes at least one warning label placed on the surgical stapler for alerting a user of the surgical stapler to the no tissue zone.

2. The system of claim 1, wherein the warning, blocking, impeding, or barrier forming device further includes a rigid shield, wherein the rigid shield is formed on or attached to the proximal end of the upper jaw.

3. The system of claim 1, wherein the warning, blocking, impeding, or barrier forming device further includes a flexible band attached to the upper jaw and to the lower jaw and extending therebetween, and wherein at least a portion of the flexible band is located in front of the second tissue stop.

4. The system of claim 1, wherein the warning, blocking, impeding, or barrier forming device further includes a curved or hinged closure link extending between the proximal end of the upper jaw and the proximal end of the lower jaw.

5. A system for preventing unwanted tissue migration in surgical staplers, comprising:
  (a) a surgical stapler having an end effector for dispensing surgical staples, wherein the end effector includes:
    (i) an upper jaw the upper jaw including a proximal end and a distal end;
    (ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
    (iii) a first tissue stop formed on the distal end of the lower jaw;
    (iv) a second tissue stop formed on the proximal end of the of the lower jaw, wherein the second tissue stop and the proximal end of the upper jaw define a no tissue zone when the surgical stapler is in an open position; and
    (v) a tissue cutting device disposed within the lower jaw for resecting tissue; and
  (b) a warning, blocking, impeding, or barrier forming device for preventing the unwanted migration of tissue into the no tissue zone during surgical procedures such that resection of unstapled tissue is prevented, wherein the warning, blocking, impeding, or barrier forming device includes a flexible sheath, wherein the flexible sheath is placed partially or completely around the proximal end of the upper jaw and the proximal end of the lower jaw while permitting opening and closing thereof.

6. A system for preventing unwanted tissue migration in surgical staplers, comprising:
  (a) a surgical stapler having an end effector for dispensing surgical staples, wherein the end effector includes:
    (i) an upper jaw the upper jaw including a proximal end and a distal end;
    (ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
    (iii) a first tissue stop formed on the distal end of the lower jaw;
    (iv) a second tissue stop formed on the proximal end of the of the lower jaw, wherein the second tissue stop and the proximal end of the upper jaw define a no tissue zone when the surgical stapler is in an open position; and
    (v) a tissue cutting device disposed within the lower jaw for resecting tissue; and
  (b) a warning, blocking, impeding, or barrier forming device for preventing the unwanted migration of tissue into the no tissue zone during surgical procedures such that resection of unstapled tissue is prevented, wherein the warning, blocking, impeding, or barrier forming device includes a post extending between the upper jaw and the lower jaw at a front end of the second tissue stop, wherein the post either rotates or telescopes when the upper jaw and the lower jaw open and close.

7. A system for preventing unwanted tissue migration in surgical staplers, comprising:
  (a) a surgical stapler having an end effector for dispensing surgical staples, wherein the end effector includes:
    (i) an upper jaw the upper jaw including a proximal end and a distal end;
    (ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
    (iii) a first tissue stop formed on the distal end of the lower jaw;
    (iv) a second tissue stop formed on the proximal end of the of the lower jaw, wherein the second tissue stop and the proximal end of the upper jaw define a no tissue zone when the surgical stapler is in an open position; and
    (v) a tissue cutting device disposed within the lower jaw for resecting tissue; and
  (b) a warning, blocking, impeding, or barrier forming device for preventing the unwanted migration of tissue into the no tissue zone during surgical procedures such that resection of unstapled tissue is prevented, wherein the warning, blocking, impeding, or barrier forming device includes a sacrificial band of compliant material, block of compliant material, or compliant balloon positioned between the proximal end of the upper jaw and the proximal end of the lower jaw.

8. A system for preventing unwanted tissue migration in surgical staplers, comprising: The system of claim 1,
  (a) a surgical stapler having an end effector for dispensing surgical staples, wherein the end effector includes:
    (i) an upper jaw the upper jaw including a proximal end and a distal end;
    (ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
    (iii) a first tissue stop formed on the distal end of the lower jaw;
    (iv) a second tissue stop formed on the proximal end of the of the lower jaw, wherein the second tissue stop and the proximal end of the upper jaw define a no tissue zone when the surgical stapler is in an open position; and
    (v) a tissue cutting device disposed within the lower jaw for resecting tissue; and
  (b) a warning, blocking, impeding, or barrier forming device for preventing the unwanted migration of tissue into the no tissue zone during surgical procedures such that resection of unstapled tissue is prevented, wherein the warning, blocking, impeding, or barrier forming device includes a non-sacrificial block of rigid material or piece of expandable material positioned between the proximal end of the upper jaw and the proximal end of the lower jaw and adapted to permit the tissue cutting device to pass therethrough.

9. A system for preventing unwanted tissue migration in surgical staplers, comprising:
   (a) a surgical stapler having an end effector for dispensing surgical staples, wherein the end effector includes:
      (i) an upper jaw the upper jaw including a proximal end and a distal end;
      (ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
      (iii) a first tissue stop formed on the distal end of the lower jaw;
      (iv) a second tissue stop formed on the proximal end of the of the lower jaw, wherein the second tissue stop and the proximal end of the upper jaw define a no tissue zone when the surgical stapler is in an open position; and
      (v) a tissue cutting device disposed within the lower jaw for resecting tissue; and
   (b) a mechanism for preventing the unwanted migration of tissue into the no tissue zone during surgical procedures such that resection of unstapled tissue is prevented, wherein the mechanism stops the tissue cutting device before it reaches the no tissue zone and reverses its direction of travel toward the distal end of the lower jaw.

10. A system for preventing unwanted tissue migration in surgical staplers, comprising:
    (a) a surgical stapler having an end effector for dispensing surgical staples, wherein the end effector includes:
       (i) an upper jaw the upper jaw including a proximal end and a distal end;
       (ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
       (iii) a first tissue stop formed on the distal end of the lower jaw;
       (iv) a second tissue stop formed on the proximal end of the of the lower jaw, wherein the second tissue stop and the proximal end of the upper jaw define a no tissue zone when the surgical stapler is in an open position; and
       (v) a tissue cutting device disposed within the lower jaw for resecting tissue; and
    (b) a mechanism for preventing the unwanted migration of tissue into the no tissue zone during surgical procedures such that resection of unstapled tissue is prevented, wherein the mechanism uses software or software and sensors associated with operation of the surgical stapler for detecting a presence of tissue within the no tissue zone and taking corrective action.

11. The system of claim 10, wherein the mechanism disengages the tissue cutting device before it reaches the no tissue zone.

12. The system of claim 10, further comprising audible, visual, or tactile indicators, or combinations thereof, that are triggered by the software or software and sensors when the presence of tissue is detected within the no tissue zone.

13. A method for preventing unwanted tissue migration in a surgical stapler having an end effector for dispensing surgical staples, wherein the end effector includes an upper jaw having proximal end and a distal end; a lower jaw having a proximal end and a distal end, wherein the distal end of the upper jaw is connected to the distal end of the lower jaw, and wherein the proximal end of the upper jaw is connected to the proximal end of the lower jaw; a first tissue stop formed on the distal end of the lower jaw; a second tissue stop formed on the proximal end of the of the lower jaw, wherein the second tissue stop and the proximal end of the upper jaw define a no cut zone when the surgical stapler is in an open position; and a tissue cutting device disposed within the lower jaw for resecting tissue, the method comprising:
   providing a warning, blocking, impeding, or barrier forming device for preventing the unwanted migration of tissue into the no tissue zone during surgical procedures such that resection of unstapled tissue is prevented; or
   providing a mechanism for preventing the unwanted migration of tissue into the no tissue zone during surgical procedures such that resection of unstapled tissue is prevented.

14. The method of claim 13, wherein the warning, blocking, impeding, or barrier forming device includes at least one warning label placed on the surgical stapler for alerting a user of the surgical stapler to the no tissue zone.

15. The method of claim 13, wherein the warning, blocking, impeding, or barrier forming device includes a flexible sheath, wherein the flexible sheath is placed partially or completely around the proximal end of the upper jaw and the proximal end of the lower jaw while permitting opening and closing thereof.

16. The method of claim 13, wherein the warning, blocking, impeding, or barrier forming device includes a rigid shield, wherein the rigid shield is formed on or attached to the proximal end of the upper jaw.

17. The method of claim 13, wherein the warning, blocking, impeding, or barrier forming device includes a flexible band attached to the upper jaw and to the lower jaw and extending therebetween, and wherein at least a portion of the flexible band is located in front of the second tissue stop.

18. The method of claim 13, wherein the warning, blocking, impeding, or barrier forming device includes a post extending between the upper jaw and the lower jaw at a front end of the second tissue stop, wherein the post either rotates or telescopes when the upper jaw and the lower jaw open and close.

19. The method of claim 13, wherein the warning, blocking, impeding, or barrier forming device includes a curved or hinged closure link extending between the proximal end of the upper jaw and the proximal end of the lower jaw.

20. The method of claim 13, wherein the warning, blocking, impeding, or barrier forming device includes a sacrificial band of compliant material, block of compliant material, or compliant balloon positioned between the proximal end of the upper jaw and the proximal end of the lower jaw.

21. The method of claim 13, wherein the warning, blocking, impeding, or barrier forming device includes a non-sacrificial block of rigid material or piece of expandable material positioned between the proximal end of the upper jaw and the proximal end of the lower jaw and adapted to permit the tissue cutting device to pass therethrough.

22. The method of claim 13, wherein the mechanism disengages the tissue cutting device before it reaches the no tissue zone.

23. The method of claim 13, wherein the mechanism stops the tissue cutting device before it reaches the no tissue zone and reverses its direction of travel toward the distal end of the lower jaw.

24. The method of claim 13, wherein the mechanism uses software or software and sensors associated with operation of the surgical stapler for detecting a presence of tissue within the no tissue zone and taking corrective action.

25. The method of claim 24, further comprising providing audible, visual, or tactile indicators, or combinations thereof, that are triggered by the software or software and sensors when the presence of tissue is detected within the no tissue zone.

\* \* \* \* \*